United States Patent
Horne et al.

(12) 
(10) Patent No.: US 6,399,767 B1
(45) Date of Patent: Jun. 4, 2002

(54) INTERMEDIATES FOR THE SYNTHESIS OF VITAMIN D AND STEROID DERIVATIVES AND PROCESS FOR PREPARATION THEREOF

(75) Inventors: David A. Horne, New York, NY (US); Noboru Kubodera, Tokyo (JP); Hiroshi Suzuki, Tokyo (JP); Hitoshi Shimizu, Tokyo (JP)

(73) Assignees: The Trustees of Columbia University in the City of New York, New York, NY (US); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/576,543

(22) Filed: May 22, 2000

Related U.S. Application Data

(63) Continuation of application No. 09/254,271, filed as application No. PCT/US97/15393 on Sep. 3, 1997, now abandoned.

(60) Provisional application No. 60/025,361, filed on Sep. 3, 1996.

(51) Int. Cl.[7] .................. C07C 403/00; C07D 303/00; C07J 17/00

(52) U.S. Cl. .............. 540/114; 549/512; 549/513; 549/516; 549/522; 552/653

(58) Field of Search ................ 549/512, 513, 549/516, 522; 540/114; 552/653

(56) References Cited

U.S. PATENT DOCUMENTS

| | | | |
|---|---|---|---|
| 4,891,364 A | | 1/1990 | Kubodera et al. |
| 5,436,401 A | * | 7/1995 | Kato et al. .................. 552/610 |
| 5,442,080 A | * | 8/1995 | Caubere et al. ............... 552/8 |
| 5,827,842 A | * | 10/1998 | Schollkopf et al. .......... 514/169 |
| 5,849,345 A | * | 12/1998 | Giger et al. ................... 426/2 |

FOREIGN PATENT DOCUMENTS

| | | |
|---|---|---|
| JP | 8-113559 | 5/1996 |
| WO | WO 9221695 | * 12/1992 |

OTHER PUBLICATIONS

Kubodera et al., Bioorg. Med. Chem. Letts., vol. 4(5), pp. 753–756, 1994.*

Watanabe et al., Chem. Pharm. Bull., vol 44(12), pp. 2280–2286, 1996.*

Kubodera et al, Synthesis of Postulated Metabolites of 1α, 25–dihydroxy–22–oxavitamin $D_3$, *Bioorganic & Medicinal Chemistry Letters*, 4(5):753–756 (1994).

Watanabe et al, Synthetic Studies of Vitamin D Analogs, XXII. Synthesis and Antiproliferation Activity of Putative Metabolites of 1α, 25–Dihydroxy–22–oxavitamin $D_3$, Chem. Pharm. Bull. 44(12):2280–2286 (1996).

Patent Abstracts of Japan,, 18(656):C1286 (1994): JP 06–256300 (Chugai Pharmaceutical Co. Ltd.—13SE1994).

* cited by examiner

*Primary Examiner*—Barbara P. Badio
(74) *Attorney, Agent, or Firm*—Browdy and Neimark, P.L.L.C.

(57) ABSTRACT

A process for preparing a compound having structure (I) wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is a CD ring structure, a steroid structure, or a vitamin D structure, each of which optionally having structure (IV) wherein W, X, Y and Z are defined above, in the presence of a base, with a compound having structure (V) or (v') wherein n, $R_1$ and $R_2$ are as defined above, and E is an eliminating group.

30 Claims, No Drawings

INTERMEDIATES FOR THE SYNTHESIS OF VITAMIN D AND STEROID DERIVATIVES AND PROCESS FOR PREPARATION THEREOF

CROSS-REFERENCE TO RELATED APPLICATIONS

The present application is a continuation of U.S. application Ser. No. 09/254,271, filed Mar. 3, 1999, now abandoned, which is a 371 of PCT/US97/15393, filed Sep. 3, 1997, which claims priority from U.S. provisional application No. 60/025,361, filed Sep. 3, 1996.

Throughout this application, various publications are referred to. Disclosures of these publications in their entireties are hereby incorporated by reference into this application to more fully describe the state of the art to which this invention pertains.

BACKGROUND OF THE INVENTION

Vitamin D and its derivatives have important physiological functions. For example, $1\alpha,25$-dihydroxy vitamin $D_3$ exhibits a broad range of physiological functions such as calcium metabolism-controlling activity, growth-inhibiting activity, differentiation-inducing activity on cells such as tumor cells, and immune-controlling activity. However, vitamin $D_3$ derivatives exhibit undesirable side effects such as hypercalcemia.

Novel vitamin D derivatives have been developed to retain effectiveness in the treatment of specific diseases while reducing associated side effects.

For example, Japanese Patent No. 61-267550 (issued Nov. 27, 1986) discloses a 9,10-seco-5,7,10(19)-pregnatriene derivative which exhibits an immune-controlling activity and a differentiation-inducing activity on tumor cells. In addition, Japanese Patent No. 61-267550 (issued Nov. 27, 1986) also discloses two processes for preparing the final product, one using pregnenorone and the other dehydroepiandorosterone as the starting material.

$1\alpha,25$-dihydroxy-22-oxavitamin $D_3$ (OCT), the 22-oxa analogue of $1\alpha,25$-dihydroxyvitamin $D_3$ has potent in vitro differentiation-inducing activities with low in vivo calcemic liability. OCT is being clinically investigated as a candidate for treatment of secondary hyperparathyroidism and psoriasis.

Japanese Patent No. 6-072994 (issued Mar. 15, 1994) discloses a 22-oxacholecalciferol derivative and a process for the preparation thereof. It discloses a process for preparing an oxacholecalciferol derivative which comprises reacting a pregnene derivative having a hydroxyl group at the 20-position with a dialkylacrylamide compound to give an ether compound and then reacting the thus-obtained ether compound with an organometal compound to give the desired compound.

Japanese Patent No. 6-080626 (issued Mar. 22, 1994) discloses a 22-oxavitamin D derivative. It also discloses a process which comprises reacting $1\alpha,3\beta$-bis(tert-butyldimethylsilyloxy)-pregne-5,7-diene-20(S or R)-ol as a starting compound with an epoxide in the presence of a base to give a compound having an ether bond at the 20-position.

In addition, Japanese Patent No. 6-256300 (issued Sep. 13, 1994) and Kubodera et al. (Bioorganic & Medicinal Chemistry Letters, 4(5): 753–756, 1994) disclose a process for stereospecifically preparing an epoxy compound which comprises reacting $1\alpha,3\beta$-bis(tert-butyldimethylsilyloxy)-pregna-5,7-diene-20(S)-ol with 4-(tetrahydropyran-2-yloxy)-3-methyl-2-butene-1-bromide to give an ether compound, deprotecting it, and subjecting the deprotected ether compound to Sharpless oxidation. However, the above processes require more than one step for introducing an ether bond and an epoxy group into a side chain of a steroid group and therefore, result in low yield of the desired compound.

Furthermore, none of the above references disclose a synthesis method in which an alcohol compound is reacted with an epoxy hydrocarbon compound having an eliminating group at its end, thereby forming an ether bond. Also, the above references do not disclose a bicyclo[4.3.0]nonane structure (hereinafter referred to as a CD ring structure), a steroid structure, or a vitamin D structure, each having an ether bond and an epoxy group at a side chain.

SUMMARY OF THE INVENTION

The present invention provides a process for preparing a compound having the structure of the following formula I:

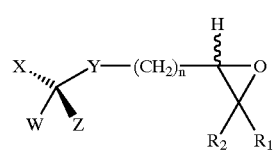

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is:

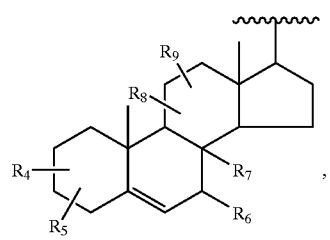

,

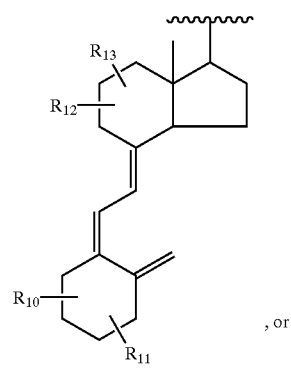

, or

-continued

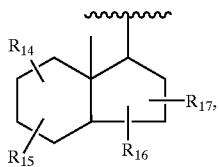

where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond; which comprises:

(a) reacting a compound having the following formula IV:

IV wherein W, X, Y and Z are as defined above, in the presence of a base, with a compound having the structure, of the following formula V or V':

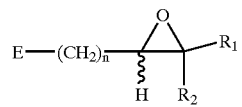

V

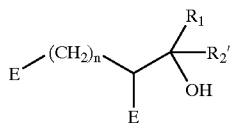

V' wherein n, $R_1$ and $R_2$ are as defined above, and E is an eliminating group, to produce the compound of formula I; and (b) recovering the compound so produced.

The present invention also provides a compound having the structure of the formula I:

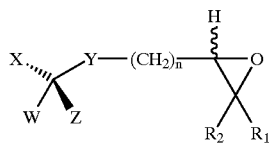

I wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is:

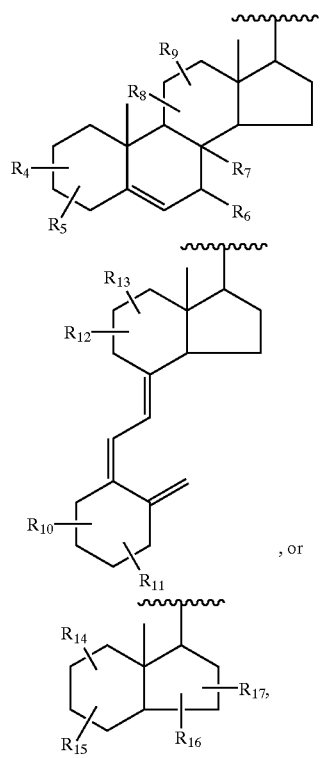

, or where each of $R_4$, $R_5$; $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond.

The present invention further provides a process for preparing a compound having the structure of the following formula VI:

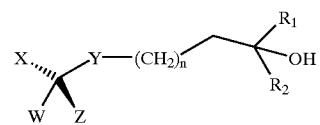

VI wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is:

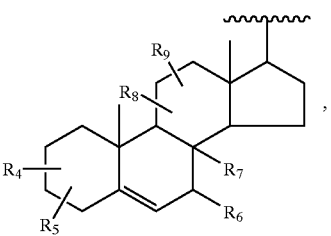

-continued

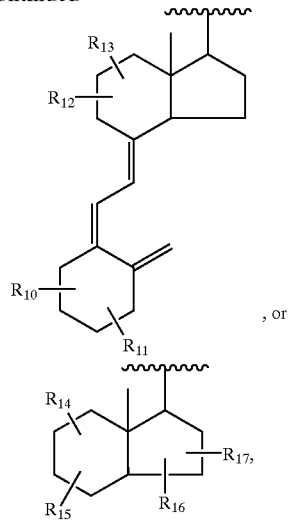
, or where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond; which comprises:

(a) reacting a compound having the following formula IV:

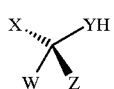
IV wherein W, X, Y and Z are as defined above, in the presence of a base, with a compound having the structure of the following formula V or formula V':

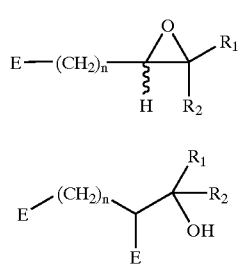
V

V' wherein n, $R_1$ and $R_2$ are as defined above, and E is an eliminating group, to produce an epoxide compound having the structure of formula I:

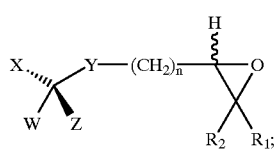
I (b) treating the epoxide compound with a reducing agent to produce the compound of formula VI; and
(c) recovering the compound so produced.

The present invention further provides a process for preparing a compound having the structure:

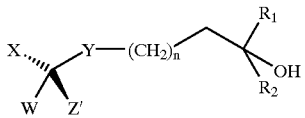

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z' is a vitamin D structure optionally having one or more protected or unprotected substituents and/or one or more protective groups, wherein Z' is preferably:

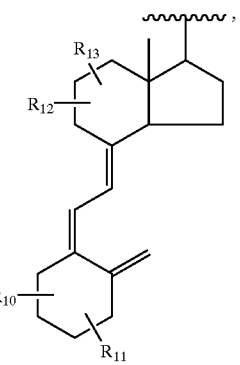

where each of $R_{10}$, $R_{11}$, $R_{12}$, and $R_{13}$ independently is hydrogen, a substituted or unsubstituted lower alkyloxy, amino, alkyl, alkylidene, carbonyl, oxo, hydroxyl, or protected hydroxyl;
which comprises:

(a) reacting a compound having the structure:

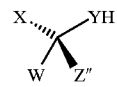

wherein W, X, and Y are as defined above and Z" represents a steroid structure optionally having one or more protected or unprotected substituents and/or one or more protective groups, Z" most preferably being:

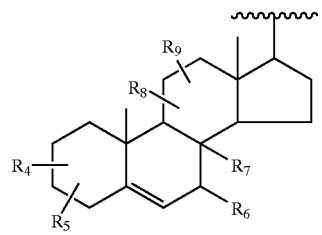

where each of $R_4$, $R_5$, $R_8$, and $R_9$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond, in the presence of a base, with a compound having the structure:

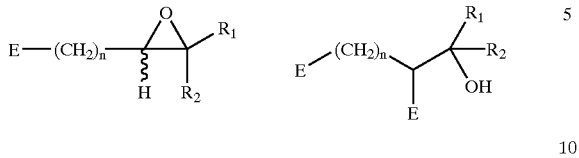

wherein n, $R_1$ and $R_2$ are as defined above, and E is an eliminating group, to produce an epoxide compound having the structure:

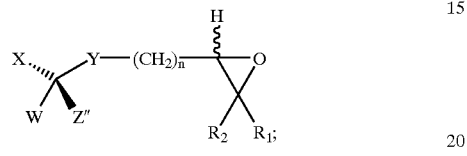

(b) treating the thus obtained epoxide compound with a reducing agent to produce the reduced compound VI;
(c) subjecting the thus obtained reduced steroid compound to ultraviolet irradiation and heat isomerization under conditions permitting the steroid structure of $Z''$ to be converted to the vitamin D structure of $Z'$; and
(d) recovering the compound so produced.

The present invention further provides a process for preparing a compound having the structure:

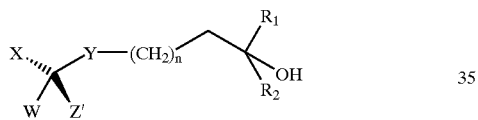

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and $Z'$ is a vitamin D structure optionally having one or more protected or unprotected substituents and/or one or more protective groups, wherein $Z'$ is preferably:

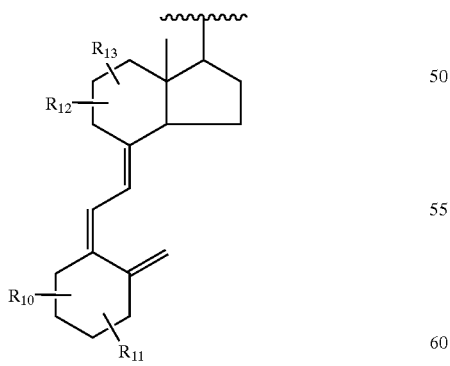

where each of $R_{10}$, $R_{11}$, $R_{12}$, and $R_{13}$ independently is hydrogen, a substituted or unsubstituted lower alkyloxy, amino, alkyl, alkylidene, carbonyl, oxo, hydroxyl, or protected hydroxyl;
which comprises:

(a) reacting a compound having the structure:

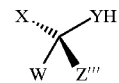

wherein W, X, and Y are as defined above and $Z'''$ represents a CD ring structure optionally having one or more protected or unprotected substituents and/or one or more protective groups, $Z'''$ most preferably being:

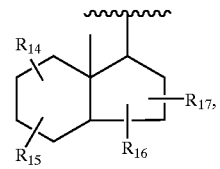

where each of $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl, in the presence of a base, with a compound having the structure:

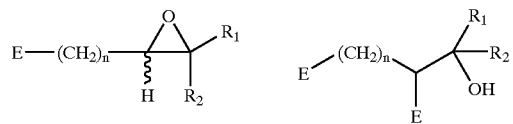

wherein n, $R_1$ and $R_2$ are as defined above, and E is an eliminating group, to produce an epoxide compound having the structure:

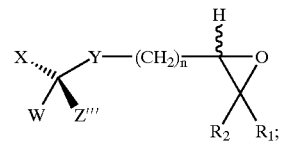

(b) treating the thus obtained epoxide compound with a reducing agent to produce the reduced compound;
(c) reacting the thus obtained reduced CD ring compound with a building block capable of producing the ring structure of vitamin D under conditions permitting the CD structure of $Z'''$ to be converted to the vitamin D structure of $Z'$; and
(d) recovering the compound so produced.

DETAILED DESCRIPTION OF THE INVENTION

The present invention provides a process for preparing a compound having the structure:

I

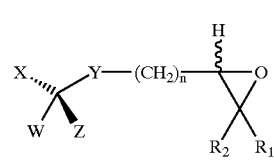

wherein n is an integer from 1–5; each of $R_1$ and $R_2$ independently is optionally substituted $C_1$–$C_6$ alkyl;

each of W and X is independently hydrogen or $C_1$–$C_6$ alkyl; Y is O, S or $NR_3$ where $R_3$ is hydrogen, $C_1$–$C_6$ alkyl or a protective group; and Z is:

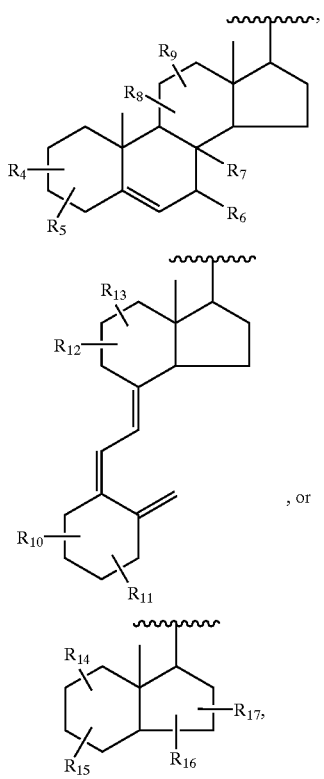
, or where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond; which comprises:

(a) reacting a compound having the structure:

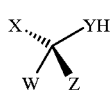
IV wherein W, X, Y and Z are as defined above, in the presence of a base, with a compound having the structure:

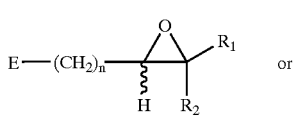
or
V

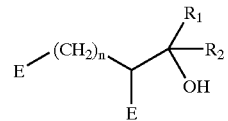
V' wherein n, $R_1$ and $R_2$ are as defined above, and E is an eliminating group, to produce the compound; and (b) recovering the compound so produced.

The term "eliminating group" as used herein means a group capable of reacting with —YH group as defined above to eliminate HE and form —Y— bond. Exemplary eliminating groups include a halogen atom such as fluorine, chlorine, bromine or iodine, a tosyl group, a mesyl group, a trifluoromethanesulfonyl group, a methanesulfonyloxy group, a p-toluenesulfonyloxy group, and an imidate group, with a halogen atom being preferred, with a bromine atom being particularly preferred.

The process for preparing a compound having the structure:

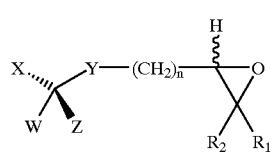
VI is novel and is useful for the synthesis of vitamin D derivatives which can have a variety of physiological activities such as differentiation-inducing activity and a growth-inhibiting activity on cells.

The present invention also provides that in the compounds having the structure:

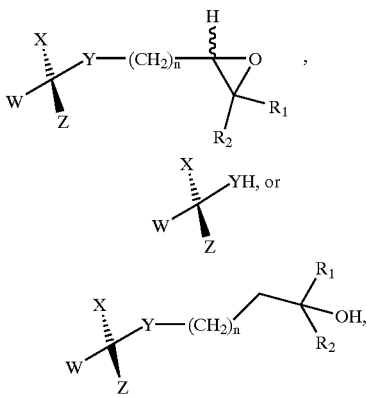

Z represents a CD ring structure, a steroid structure or a vitamin D structure, each of which optionally has one or more protected or unprotected substituents and/or more protective groups. Each of the CD ring structure, steroid structure and vitamin D structure for the present invention particularly means a structure as described below, any ring of which may optionally have one or more unsaturated bonds. In the steroid structure, one having one or two unsaturated bonds are preferred, and 5-ene steroid compound, 5,7-diene steroid compound, or a protected compound thereof, are particularly preferred.

CD ring structure:

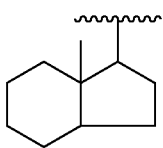

Steroid structures:

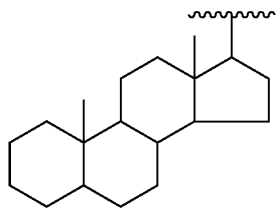

Vitamin D structure:

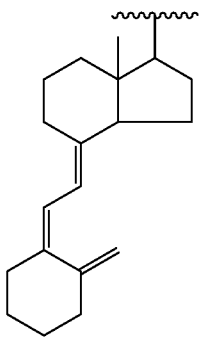

The substituents on Z which is the CD structure, steroid structure, or vitamin D structure are not particularly limited but may be exemplified by a hydroxyl group, a substituted or unsubstituted lower alkyloxy group, a substituted or unsubstituted amino group, a substituted or unsubstituted alkyl group, a substituted or unsubstituted alkylidene group, a carbonyl group and an oxo group (=O), with a hydroxyl group being preferred. These substituents may be protected. Useful protective groups are not particularly limited but include an acyl group, a substituted silyl group and a substituted or unsubstituted alkyl group, with an acyl group and a substituted silyl group being preferred. Examples of the acyl group include an acetyl group, a benzoyl group, a substituted acetyl group and a substituted benzoyl group, as well as carbonate types and carbamate types, with an acetyl group being preferred. Examples of substituents on the said acetyl and benzoyl groups include a halogen atom, an alkyl group, an alkenyl group and an aryl group, with a fluorine atom, a chlorine atom, a methyl group, a phenyl group and an ethylidene group being preferred. Preferred examples of the substituted acetyl group include a chloroacetyl group, a trifluoracetyl group, a pivaloyl group and a crotonoyl group. Preferred examples of the substituted benzoyl group include a p-phenylbenzoyl group and a 2,4,6-trimethylbenzoyl group. Examples of the substituted silyl group include a trimethylsilyl group, a triethylsilyl group, a triisopropylsilyl group, a tert-butyldimethylsilyl (TBS) group and a tert-butyldiphenylsilyl group, with a tert-butyldimethylsilyl (TBS) group being preferred. Examples of the substituted or unsubstituted alkyl group include a methyl group, a meth-oxymethyl group, a methylthiomethyl group, tert-butylthiomethyl group, a benzyloxymethyl group, a p-methoxybenzyloxymethyl group, a 2-methoxyethoxymethyl group, a tetrahydropyranyl group, a tert-butyl group, an allyl group, a benzyl group, a p-methoxybenzyl group, and an o- or p-nitrobenzyl group.

Examples of a protective group for an unsaturated bond in the steroid structure include 4-phenyl-1,2,4-triazoline-3,5-dione and diethyl maleate. An example of adducts having such protective group is the following:

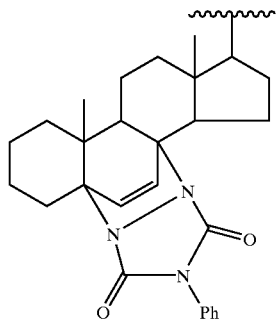

Furthermore, the vitamin D structure may be protected by addition of $SO_2$. Examples of such protected vitamin D structures are given below:

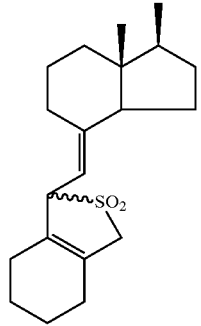

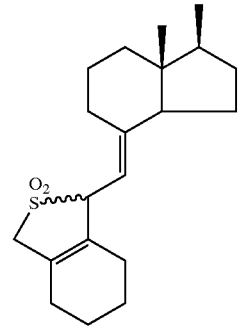

In the formulae I, V, V' and VI according to the present invention, $R_1$ and $R_2$, which may be the same or different, each represents a substituted or unsubstituted lower alkyl group, with an unsubstituted lower alkyl group being preferred. In the definition of $R_1$ and $R_2$, the lower alkyl group means a straight or branched alkyl group having 1–6 carbon atoms. Examples of the lower alkyl group include a methyl group, an ethyl group, a n-propyl group, an i-propyl group, a n-butyl group, a s-butyl group, and a t-butyl group, with a methyl group and an ethyl group being particularly preferred. In the definition of $R_1$ and $R_2$, the substituents on the substituted alkyl group may be exemplified by a hydroxyl group and an amino group, with a hydroxyl group being preferred.

In the formulae I, IV and VI according to the present invention, W and X, which may be the same or different, each represents a hydrogen atom or a straight or branched lower alkyl group. Preferably, one of W and X is an alkyl group, most preferably a methyl group, and the other is a hydrogen atom. Particularly preferably, W is a methyl group and X is a hydrogen atom.

In the formulae I, IV and VI according to the present invention, Y represents O, S or $NR_3$ wherein $R_3$ represents a hydrogen atom or a protective group. Examples of the protective group in $R_3$ include a substituted or unsubstituted carbamate group, a substituted or unsubstituted amide group and a substituted or unsubstituted alkyl group, alkyl preferably being $C_1$–$C_6$ alkyl, with a methyl carbamate group, an ethyl carbamate group, a trichloroethylcarbamate group, a t-butylcarbamate group, a benzylcarbamate group, an acetoamide group, a trifluoroacetoamide group, a methyl group and a benzyl group being preferred. Y is preferably O or S, with O being particularly preferred.

In the formulae I, V, V' and VI according to the present invention, n is 1, 2, 3 or 4, preferably 1 or 2, particularly preferably 1. Preferably, when n is 1 and where one of $R_1$ and $R_2$ is a methyl group, the other is not a hydroxymethyl group.

A particularly preferred embodiment of the compound represented by the formula I according to the present invention is such that the formula I, $R_1$ and $R_2$ are the same and each represents a methyl group or an ethyl group, W and X are different and each represents a hydrogen atom or a methyl group, Y represents O, and n represents 1 or 2.

The more preferred examples of the compound represented by the formula I according to the present invention are represented by the following formulae IIA and IIB:

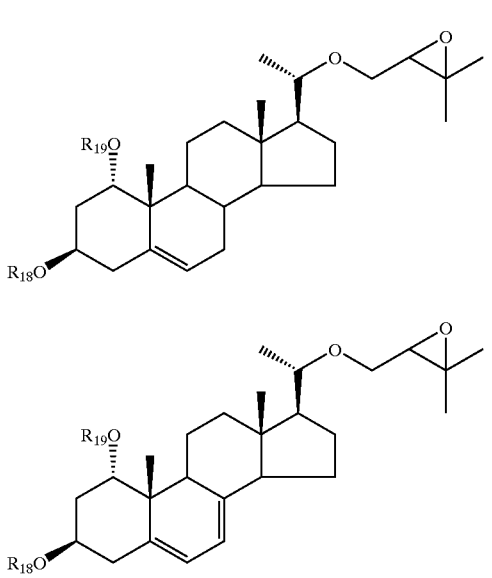

wherein $R_{18}$ and $R_{19}$, which may be the same or different, each represents a hydrogen atom or a protective group; or the following formulae IIIA and IIIB:

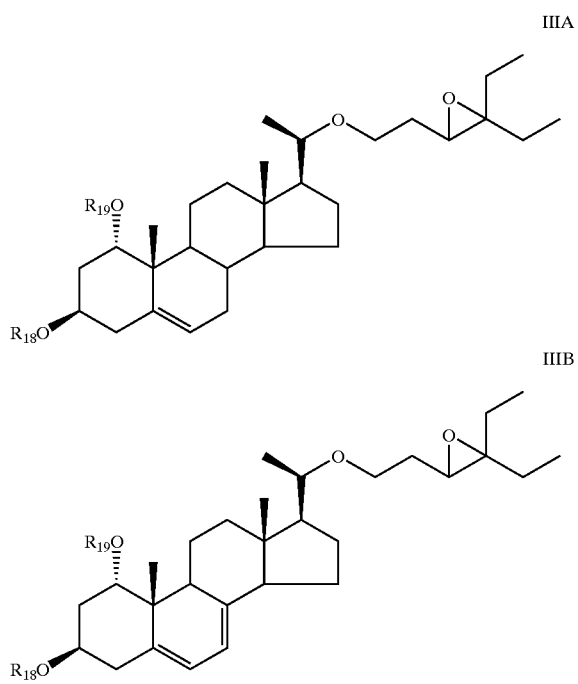

wherein $R_{18}$ and $R_{19}$, which may be the same or different, each represents a hydrogen atom or a protective group.

The most preferred example of the compound represented by the formula I according to the present invention is represented by the above formulae IIA and IIB.

An outline of the reaction disclosed herein for the production of the compound of formula I is shown in the following reaction scheme A.

Reaction Scheme A:

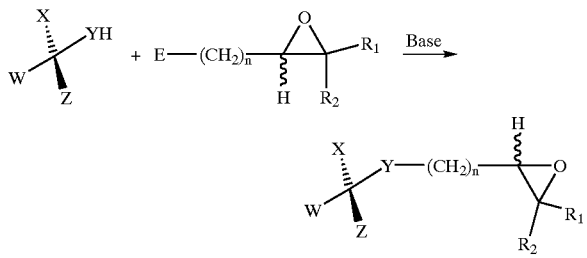

Some of the compounds which are used as a starting compound in the above-mentioned process according to the present invention, are known compounds. For example, when "Y" is O, the following can be used as the starting compounds: the 1α,3β-bis(tert-butyldimethylsilyloxy)-pregna-5,7-diene-20(S)-ol described in Japanese Patent No. 61-267550 (issued Nov. 27, 1986); the 9,10-seco-5,7,10(19)-pregnatriene-1α,3β,20β-triol optionally with the hydroxyl group being protected described in Japanese Patent No. 61-267550 (issued Nov. 27, 1986) and International Patent Publications WO 90/09991 (Sep. 7, 1990) and WO 90/09992 (Sep. 7, 1990); the octahydro-4-(t-butyldimethylsilyloxy)-7-methyl-1H-indene-1-ol described in J. Org. Chem., 57, 3173 (1992); and the octahydro-4-(acetyloxy)-7-methyl-1H-indene-1-ol described in J. Am. Chem. Soc., 104, 2945 (1982).

When "Y" is S, a starting compound (formula IV) having a thiol group (—SH-group) at 20-position may be used instead of the said compound having a hydroxyl group at 20-position. Such a compound can be obtained, for example, by converting a ketone compound to a thiol compound in accordance with a previously described method (Journal of the American Chemical Society, 102:10 [1980] pp. 3577–3583). More particularly, the ketone compound is reacted with 1 equivalent of 1,2-ethanedithiol in the presence of a catalyst to prepare the corresponding ethylene thioketal compound, and then the thus-obtained ethylene thioketal compound is reacted with 3–4 equivalents of n-butyllithium to yield the corresponding thiol compound. Alternatively, such a thiol compound can be synthesized from a compound having an aldehyde group or a protected hydroxyl group at 20-position in accordance with the method described in International Patent Publication WO 94/14766 (Jul. 7, 1994).

Furthermore, starting compounds wherein "Y" is $NR_3$ (where $R_3$ represents a hydrogen atom or a protective group), are also known and disclosed (Chem. Pharm. Bull. Vol. 32, pp. 1416–1422 [1984]).

Some of the compounds having the structure:

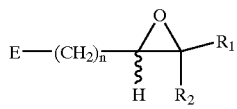

which are used as a reactant in the above-mentioned process according to the present invention, are known compounds and can be prepared in accordance with a known method by reacting an alkenyl compound having an eliminating group at its end with an organic peracid such as m-chloroperbenzoic acid (mCPBA) in an inert organic solvent. "EE" represents an eliminating group. The term "eliminating group" as used herein means a group capable of reacting with —YH group in formula IV to eliminate HE and form —Y— bond. Exemplary eliminating groups include a halogen atom such as fluorine, chlorine, bromine or iodine, a tosyl group, a mesyl group, a trifluoromethanesulfonyl group, a methanesulfonyloxy group, a p-toluenesulfonyloxy group, and an imidate group, with a halogen atom being preferred, with a bromine atom being particularly preferred.

The above-mentioned reaction (scheme A) according to the present invention is carried out in the presence of a base. Examples of the base that can be used include alkali metal hydrides, alkali metal hydroxides and alkali metal alkoxides, with alkali metal hydrides being preferred, with sodium hydride being particularly preferred.

The reaction is preferably carried out in an inert solvent. Examples of the solvent that can be used include ether solvents, saturated aliphatic hydrocarbon solvents, aromatic hydrocarbon solvents, amide solvents, and combinations thereof, with dimethylformamide (DMF), tetrahydrofuran (THF), benzene, toluene, diethyl ether, and a mixture of DMF and diethyl ether, being preferred, with dimethylformamide and tetrahydrofuran being more preferred.

The reaction temperature may appropriately be controlled, generally in the range from 25° C. to a reflux temperature of a solvent, preferably from 40° C. to 65° C.

The reaction time may appropriately be controlled, generally in the range from 1 hour to 30 hours, preferably from 2 hours to 5 hours. The progress of the reaction my be monitored by thin layer chromatography (TLC).

In one embodiment of the present invention, the process for preparing a compound having the structure:

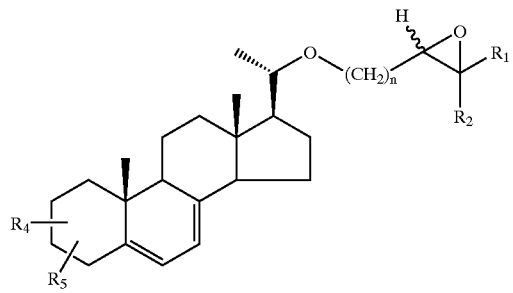

comprises:

(a) reacting a compound having the structure:

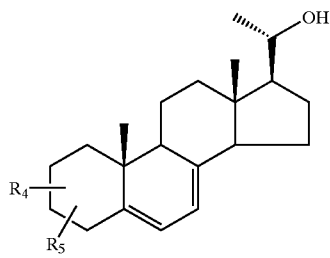

in the presence of a base, with a compound having the structure:

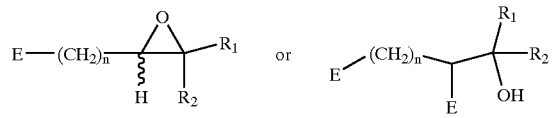

to produce the compound; and b) recovering the compound so produced.

In another embodiment of the present invention, the process for preparing a compound having the structure:

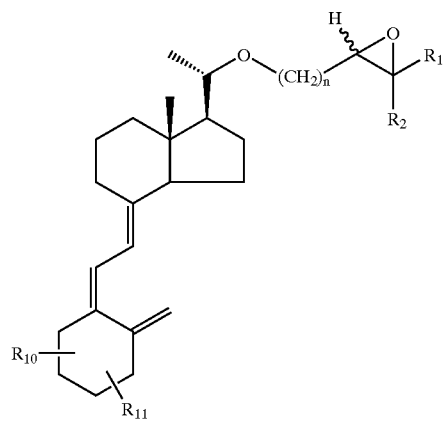

comprises:

(a) reacting a compound having the structure:

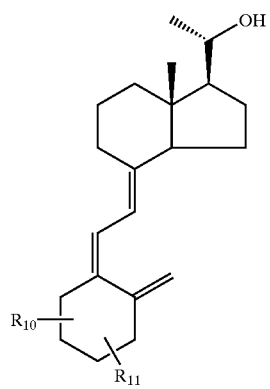

in the presence of a base, with a compound having the structure:

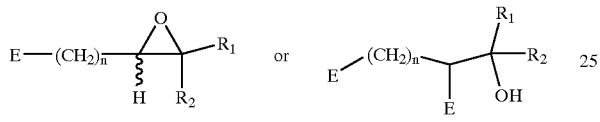

to produce the compound; and b) recovering the compound so produced.

In yet another embodiment of the present invention, the process for preparing a compound having the structure:

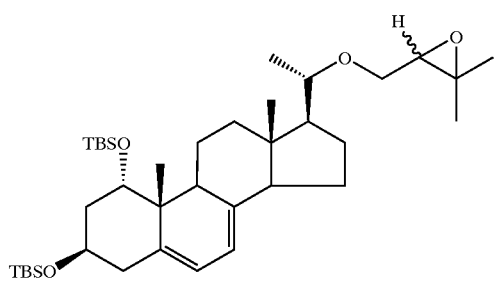

comprises:

(a) reacting a compound having the structure:

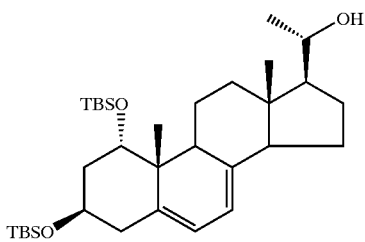

in the presence of a base, with a compound having the structure:

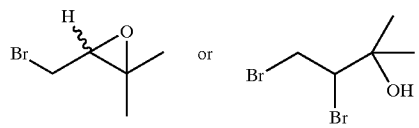

to produce the compound; and b) recovering the compound so produced.

In another embodiment of the present invention, the process for preparing a compound having the structure:

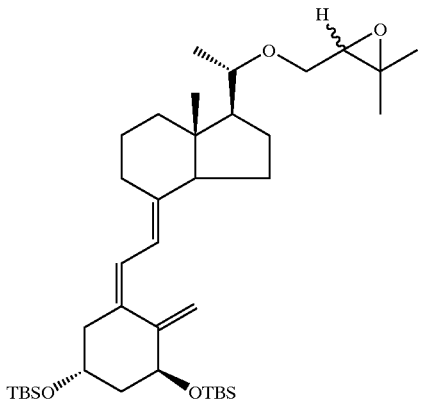

comprises:

(a) reacting a compound having the structure:

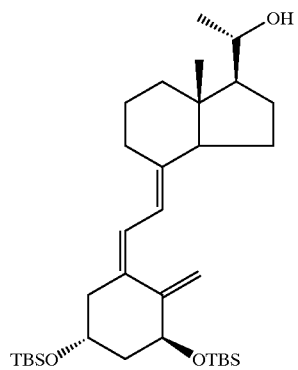

in the presence of a base, with a compound having the structure:

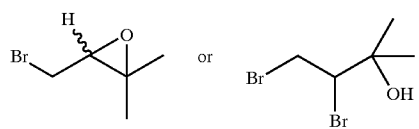

to produce the compound; and b) recovering the compound so produced.

In yet another embodiment of the present invention, recovery of the compound comprises filtration or chromatography.

In another embodiment of the present invention, the eliminating group is halogen, mesyl, tosyl, imidate, trifluoromethanesulfonyl, or phenylsulfonyl.

In yet another embodiment of the present invention, the halogen is bromine.

In another embodiment of the present invention, the base is alkali metal hydride, alkali metal hydroxide, or alkali metal alkoxide.

In yet another embodiment of the present invention, the alkali metal hydride is NaH or KH.

In another embodiment of the present invention, the base is $NaOR_{20}$, $KOR_{20}$, $R_{20}Li$, $NaN(R_{21})_2$, $KN(R_{21})_2$, or $LiN(R_{21})_2$; $R_{20}$ is alkyl; and $R_{21}$ is isopropyl or $(CH_3)_3Si$.

The present invention also provides a compound having the structure:

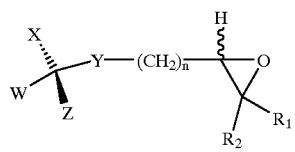

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is:

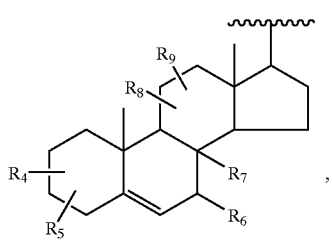

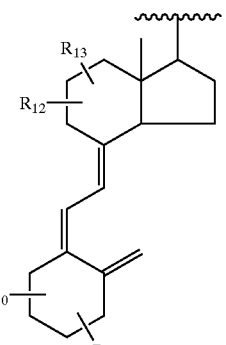

, or

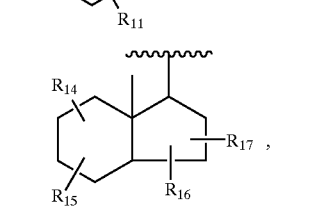

where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond.

The compound having the structure:

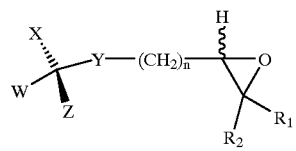

is a novel compound and a useful intermediate for the synthesis of vitamin D derivatives which can have a variety of physiological activities such as differentiation-inducing activity and a growth-inhibiting activity on cells.

In one embodiment of the present invention, the compound has the structure:

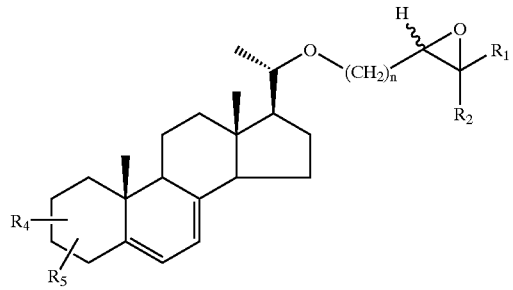

In another embodiment of the present invention, the compound has the structure:

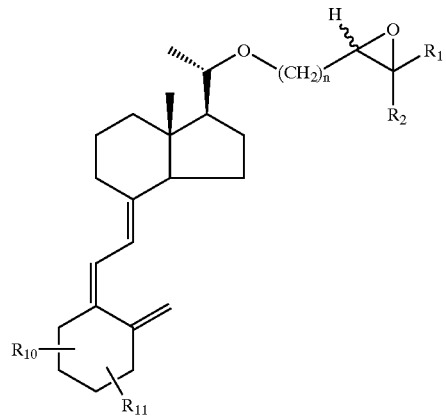

In yet another embodiment of the present invention, the compound has the structure:

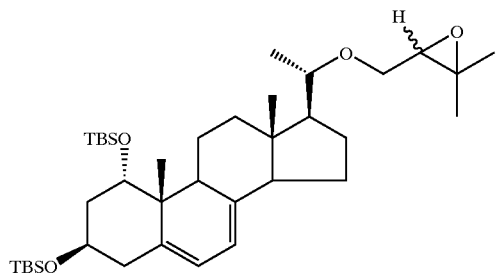

In another embodiment of the present invention, the compound has the structure:

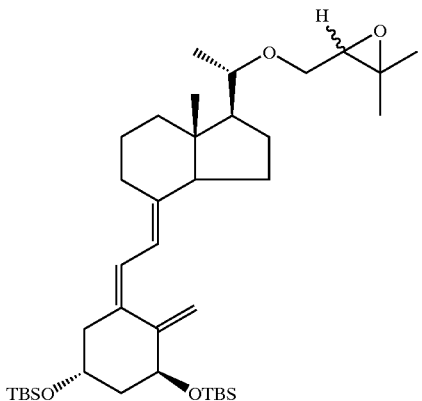

The present invention further provides a process for preparing a compound having the structure:

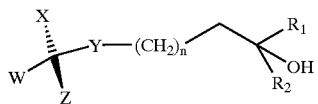

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is:

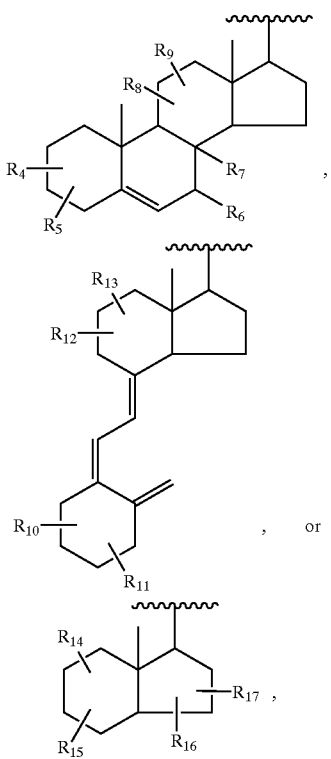

where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond; which comprises:

(a) reacting a compound having the structure:

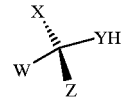

wherein W, X, Y and Z are as defined above, in the presence of a base, with a compound having the structure:

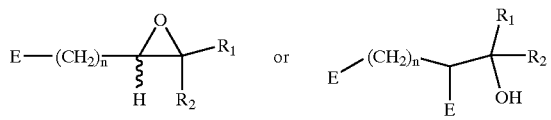

wherein n, $R_1$ and $R_2$ are as defined above, and E is an eliminating group, to produce an epoxide compound having the structure:

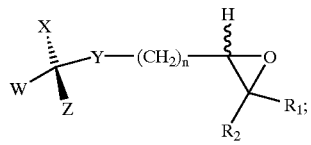

(b) treating the epoxide compound with a reducing agent to produce the compound; and
(c) recovering the compound so produced.

The present invention relates to a process for preparing vitamin D or steroid derivatives via the novel intermediates described hereinabove. An outline of this reaction is shown in the following reaction scheme B.

Reaction Scheme B:

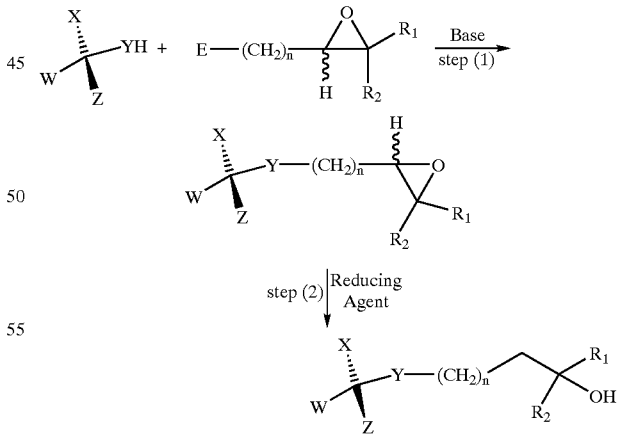

The reaction in step (1) of the above-mentioned two-step reaction according to the present invention can be carried out in the same way as in the process of Reaction Scheme A, which was already described herein.

The reaction in the step (2) is a reaction to open the epoxy ring in the epoxy compound obtained in step (1) and it is carried out using a reducing agent. The reducing agent which can be used in step (2) is such that it is capable of opening the ring of an epoxy compound obtained in step (1) to give a hydroxyl group, preferably capable of selective formation of a tertiary alcohol.

Examples of the reducing agent are listed below:
Lithium aluminumhydride [LiAlH$_4$];
Lithium triethylborohydride [LiEt$_3$BH, Super-Hydride];
Lithium tri-sec-butylborohydride [Li(s-Bu)$_3$BH, L-Selectride];
Potassium tri-sec-butylborohydride [K(s-Bu)$_3$BH, K-Selectride];
Lithium trisiamylborohydride [LiB[CH(CH$_3$)CH(CH$_3$)$_2$]$_3$H, LS-Selectride];
Potassium trisiamylborohydride [KB[CH(CH$_3$)CH(CH$_3$)$_2$]$_3$H, KB(Sia)$_3$H, KS-Selectride];
Lithium dimethylborohydride [LiB(CH$_3$)$_2$H$_2$];
Lithium thexylborohydride [Li[(CH$_3$)$_2$CHC(CH$_3$)$_2$BH$_3$];
Lithium thexyllimonylborohydride;

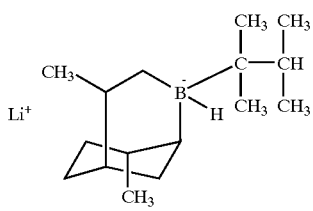

Lithium tri-tert-butoxyaluminohydride [LiAl[OC(CH$_3$)$_3$]$_3$H];
Potassium tris(3,5-dimethyl-1-pyrazolyl)borohydride;

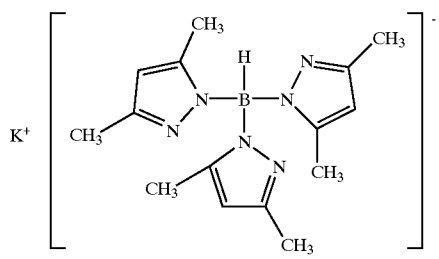

KB(C$_6$H$_5$)$_3$H;
Lithium 9-BBN hydride;

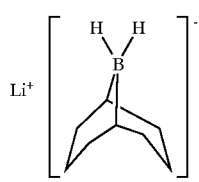

NaBH$_4$;
NaBH$_3$CN.

Moreover, an additive such as lithium salts, preferably lithium halides such as lithium bromide (LiBr) and lithium iodide (LiI), particularly preferably LiI, may be added to the reducing agent, particularly in the case where the reducing agent contains potassium.

Preferred examples of the reducing agent are listed below:
Lithium aluminumhydride [LiAlH$_4$];
Potassium tri-sec-butylborohydride [K(s-Bu)$_3$BH, L-Selectride]+LiI;
Lithium triethylborohydride [LiEt$_3$BH, Super-Hydride];
Lithium tri-sec-butylborohydride [Li(s-Bu)$_3$BH, L-Selectride];
Lithium 9-BBN hydride.

Particularly preferred examples of the reducing agents are listed below:
Lithium triethylborohydride [LiEt$_3$BH, Super-Hydride];
Lithium tri-sec-butylborohydride [Li(s-Bu)$_3$BH, L-Selectride];
Lithium 9-BBN hydride.

It is also possible to preferentially obtain a compound having a hydroxyl group at 24-position of the vitamin D compound by selecting a suitable reducing agent, such as, for example, diisobutylaluminumhydride (DIBAL-H).

The reaction in step (2) is preferably carried out in an inert solvent. Examples of the solvent that can be used include diethylether, tetrahydrofuran (THF), dimethylformamide (DMF), benzene and toluene, with diethylether and tetrahydrofuran being preferred.

The reaction temperature in step (2) may appropriately be controlled, generally in the range from 10° C. to 100° C., preferably from room temperature to 65°.

The reaction time in step (2) may appropriately be controlled, generally in the range from 30 minutes to 10 hours, preferably from 1 hour to 5 hours. The progress of the reaction can be monitored by thin layer chromatography (TLC).

The reaction in step (2) can be carried out after step (1), more specifically after the purification of the reaction product of step (1) by means of a suitable method such as silica gel chromatography, or alternatively, it can be carried out by directly adding a reducing agent to a mixture containing the reaction product of step (1) without purifying it. The process where step (2) is carried out after step (1) without purification of the product is referred to as "one-pot reaction" and this is preferred since it is operationally less tedious.

A greatly preferred and surprisingly superior one-pot reaction has been discovered which permits excellent yield of compound VI directly from compound I, without first purifying the intermediate compound IV, while using a relatively small amount of the reactant of formula V, as well as a relatively small amount of base. This improved process is obtained by using THF as the solvent. Neither DMF nor a combination of DMF and dimethyl ether will permit one-pot conversion. The choice of reducing agent is also important to achieve the best one-pot yields. For the preferred one-pot process, the preferred reducing agent is L-Selectride, K-Selectride with LiI as an additive, lithium 9-BBN hydride or Super-Hydride. LiAlH$_4$ can also be used as the reducing agent in the improved one-pot process, although one will not achieve as high a conversion to the desired product using the latter reducing agent. Using the preferred solvent (THF) and reducing agent, one can reduce the mole equivalent of base which is used in the reaction to as low as 1.5 and the mole equivalent of the reagent of formula V to the substrate to only 1.3, while still obtaining almost 100% conversion to the desired stereospecific product.

The following Reaction Scheme C shows reaction routes using the compounds and processes of the present invention. Processes for the synthesis of a vitamin D compound from the corresponding steroid compound can be carried out by a conventional process such as ultraviolet irradiation and heat isomerization. Processes for the synthesis of a vitamin D compound from the corresponding CD ring compound are also conventional. Such processes are described in, for example, E. G. Baggiolini et al., J. Am. Chem. Soc., 104, 2945–2948 (1982) and Wovkulich et al., Tetrahedron, 40, 2283 (1984). It should be understood that a part or all of the processes shown in Reaction Scheme C are embraced within the present invention.

Reaction Scheme C
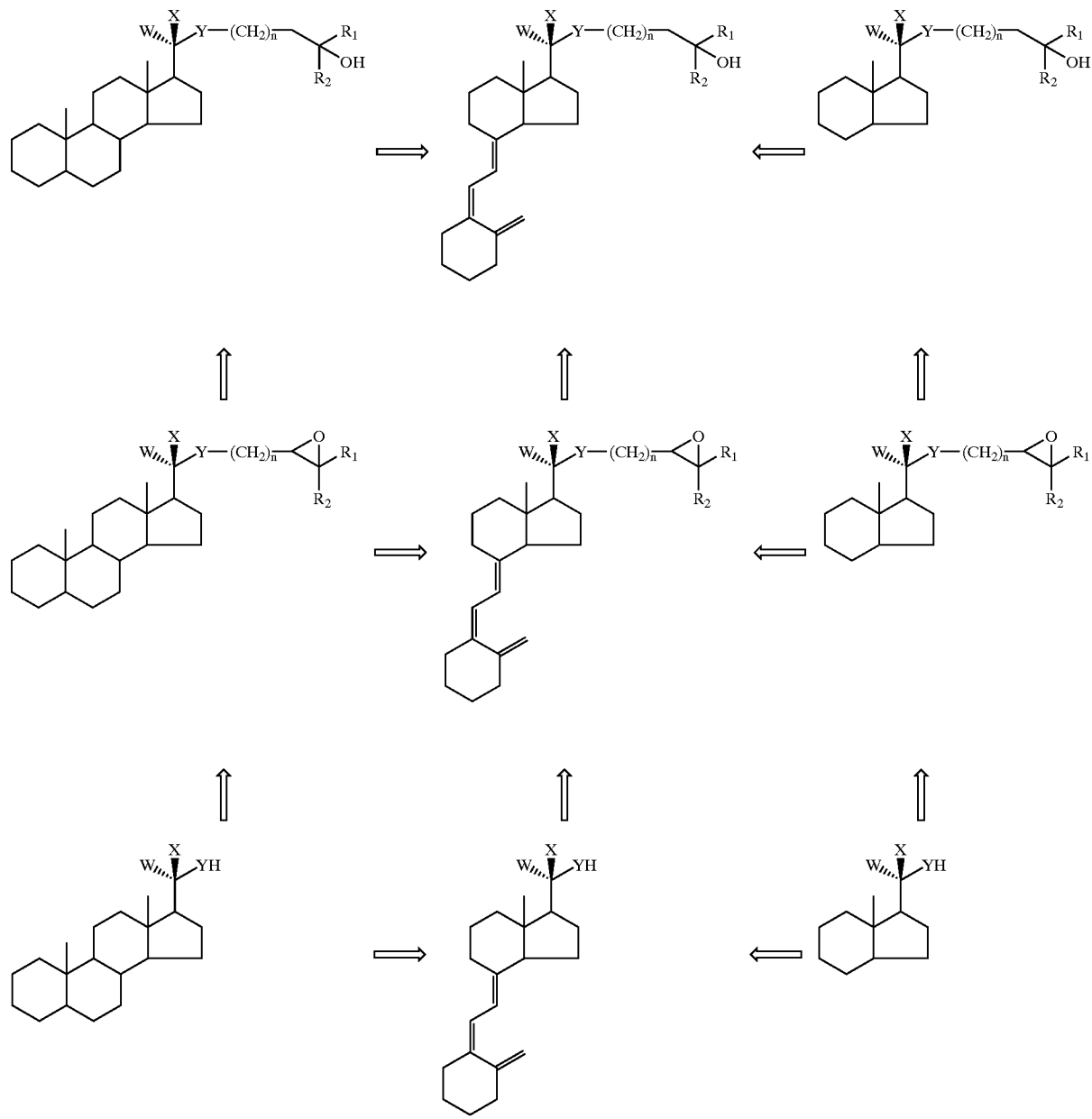
(Wherein W, X, Y, O, $R_1$, and $R_2$ are the same as defined hereinabove, and any ring of the structure may optionally have one or two unsaturated bonds).
Particularly preferred examples of the vitamin D derivatives of the final product, which can be obtained by utilizing the present invention, are represented by the following formulae VII and VIII:
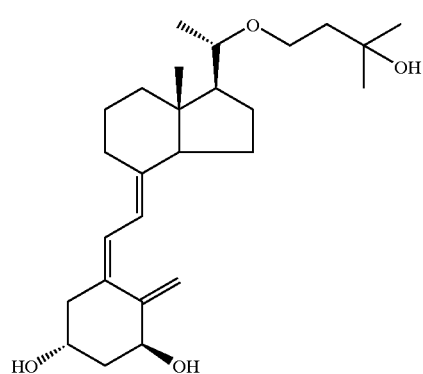
VII

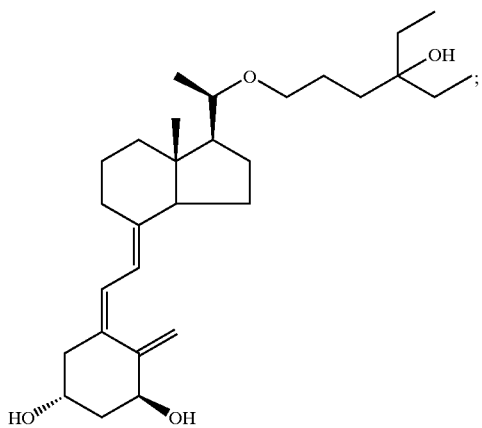

the most preferred example being represented by the formula VII.

In one preferred embodiment of the present invention, the process for preparing a compound having the structure:

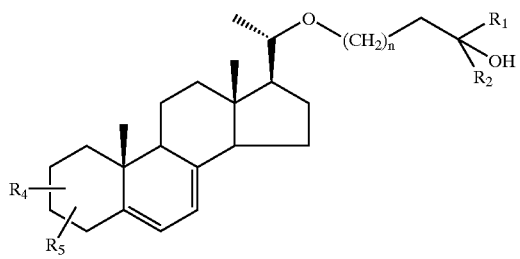

comprises:

a) reacting a compound having the structure:

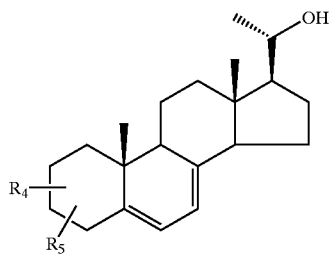

in the presence of a base, with a compound having the structure:

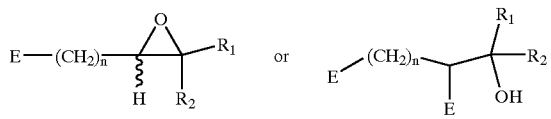

to produce an epoxide compound having the structure:

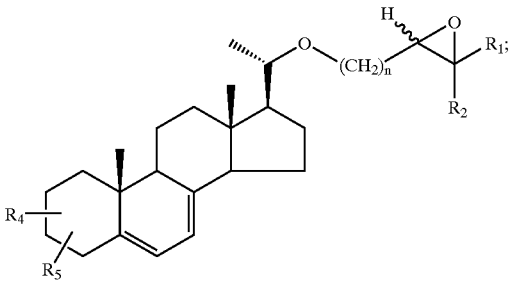

(b) treating the epoxide compound with a reducing agent to produce the compound; and (c) recovering the compound so produced.

In another embodiment of the present invention, the process for preparing a compound having the structure:

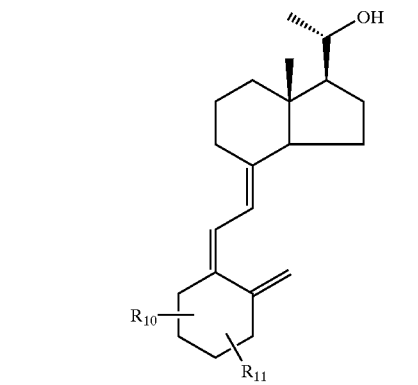

comprises:

a) reacting a compound having the structure:

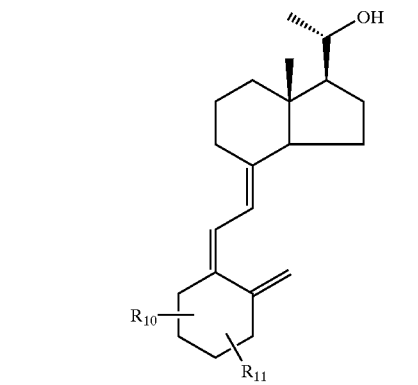

in the presence of a base, with a compound having the structure:

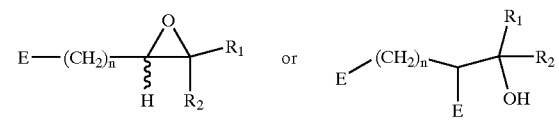

to produce an epoxide compound having the structure:

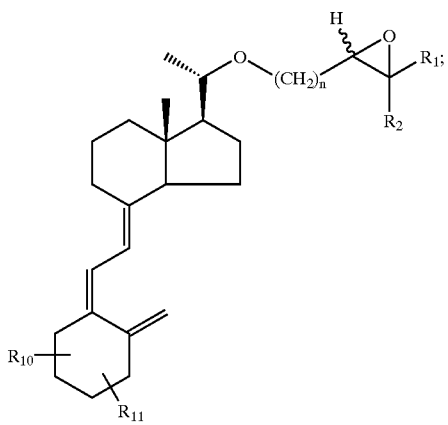

(b) treating the epoxide compound with a reducing agent to produce the compound; and (c) recovering the compound so produced.

In yet another embodiment of the present invention, the process for preparing a compound having the structure:

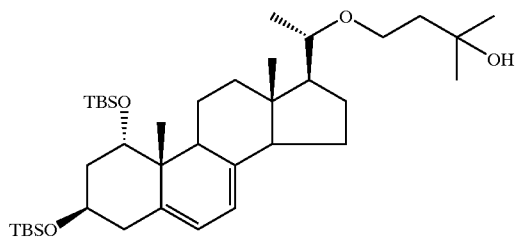

comprises:

a) reacting a compound having the structure:

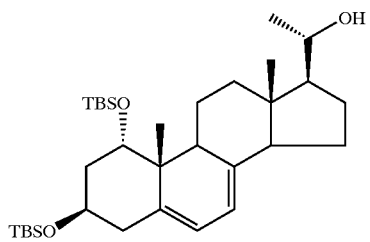

in the presence of a base, with a compound having the structure:

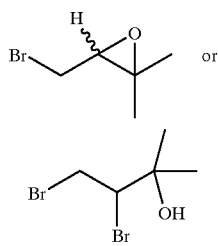

to produce an epoxide compound having the structure:

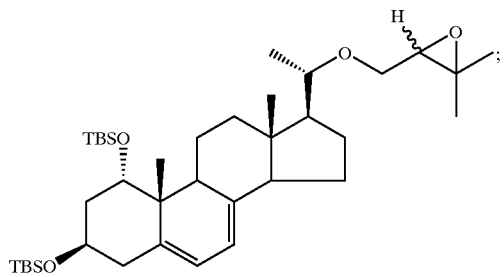

(b) treating the epoxide compound with a reducing agent to produce the compound; and (c) recovering the compound so produced.

In another embodiment of the present invention, the process for preparing a compound having the structure:

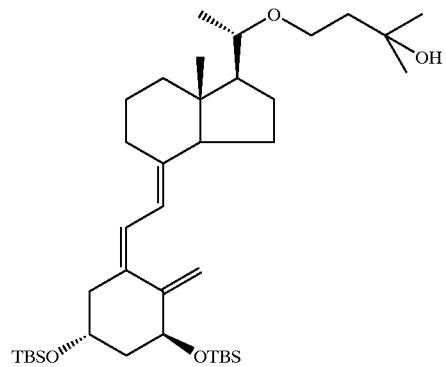

comprises reacting a compound having the structure:

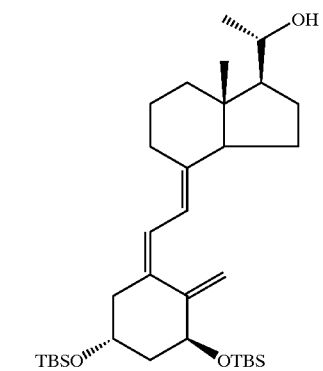

in the presence of a base, with a compound having the structure:

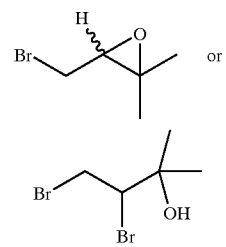

to produce an epoxide compound having the structure:

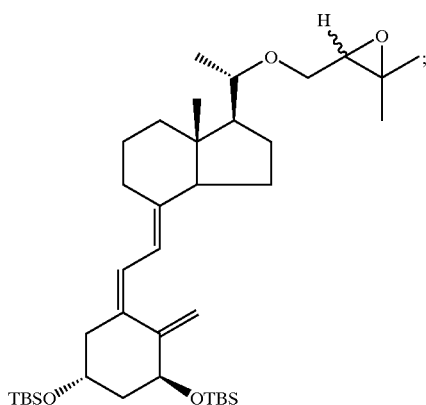

(b) treating the epoxide compound with a reducing agent to produce the compound; and (c) recovering the compound so produced.

In yet another embodiment of the present invention, recovery of the compound comprises filtration or chromatography.

In yet another embodiment of the present invention, the eliminating group is halogen, mesyl, tosyl, imidate, trifluoromethanesulfonyl, or phenylsulfonyl.

In another embodiment of the present invention, the halogen is bromine.

In yet another embodiment of the present invention, the base is alkali metal hydride, alkali metal hydroxide, or alkali metal alkoxide.

In another embodiment of the present invention, the alkali metal hydride is NaH or KH.

In yet another embodiment of the present invention, the base is $NaOR_{20}$, $KOR_{20}$, $R_{20}Li$, $NaN(R_{21})_2$, $KN(R_{21})_2$, or $LiN(R_{21})_2$; $R_{20}$ is alkyl; and $R_{21}$ is isopropyl or $(CH_3)_3Si$.

In another embodiment of the invention, the reducing agent is $LiAlH_4$, $Li(s-Bu)_3BH$, or $LiEt_3BH$.

This invention will be better understood from the Experimental Details which follow. However, one skilled in the art will readily appreciate that the specific methods and results discussed are merely illustrative of the invention as described more fully in the claims which follow thereafter.

EXAMPLE 1
Synthesis of 4-bromo-2,3-epoxy-2-methylbutane

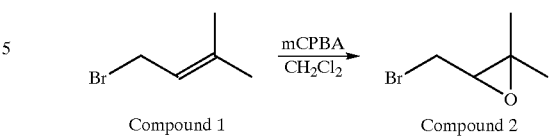

To a stirred solution of commercial (96%) 4-bromo-2-methyl-butene (Compound 1) (10 g, 0.064 moles) in 300 mL of methylene chloride ($CH_2Cl_2$) was slowly added m-chloroperbenzoic acid (mCPBA) (80–85%), 20 g, 0.093–0.099 moles) at room temperature. The reaction mixture was stirred for 1 hour and the resulting solid was removed by filtration. A 5% $Na_2S_2O_4$ solution (100 mL) was added to the filtrate and stirred for 30 min. The methylene chloride layer was then separated and washed with saturated aqueous $NaHCO_3$ (200 mL, 2×) saturated aqueous NaCl, and dried over anhydrous $MgSO_4$. After evaporation of the solvent, the remaining liquid was distilled to afford 8.9 g (85%) of the title compound (Compound 2) as a pure product [colorless liquid, bp 55° C./29 mmHG].

The proton nuclear magnetic resonance spectrum of the title compound (Compound 2) gave the following signal:

400 MHz $^1$H NMR ($CDCl_3$): δ3.52 (dd, J=10.3, 6.0 Hz, 1H), 3.27 (dd, J-10.3, 7.5 Hz, 1H), 3.09 (dd, J=7.5, 6.0 Hz, 1H), 1.37 (3, 3H), 1.33 (s, 3H).

The epoxide can be made from a dibromo compound under basic conditions (Journal of American Chemical Society, 76, p.4374; 1954). The following reaction scheme is illustrative:

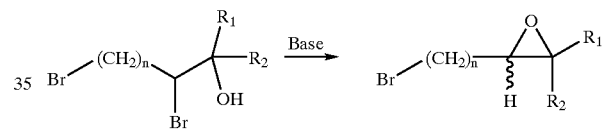

Therefore the dibromo compound in the above reaction scheme can be used instead of the epoxide compound when the reaction is under basic conditions. Other eliminating groups, as defined above, may be substituted for one or both Br atoms of the bromohydrin.

EXAMPLE 2
Synthesis of 1α,3β-bis(t-butyldimethylsilyloxy)-20 (S)-2,3-epoxy-3-methylbutyloxy)pregna-5,7-diene

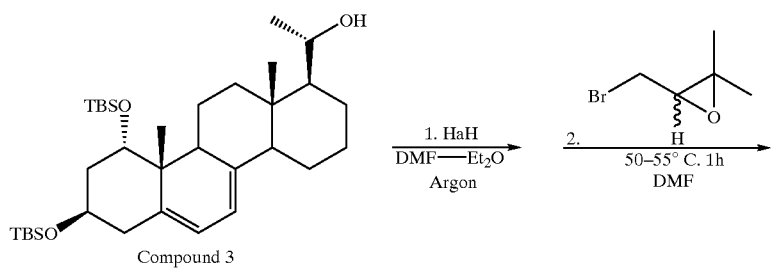

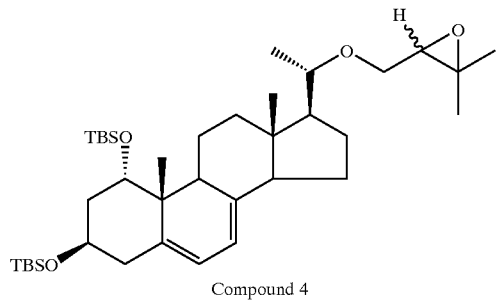

Compound 4

To a vigorously stirred solution of alcohol Compound 3 (0.5 g, 0.89 mmol) in 20 ml of DMF/diethyl ether (1:1) solution cooled in an ice-water bath was is added sodium hydride (60% oil dispersion, 0.2 g, 5.0 mmol) under argon. Additional diethyl ether (~5 ml) was added after 30 min (due to evaporation) in order to maintain a constant 1:1 DMF/diethyl ether mixture. After stirring for 1 hour, the reaction mixture was warmed to room temperature and a heavy stream of argon was blown over the vigorously stirred reaction mixture to remove the diethyl ether. Upon removal of the diethyl ether, the argon stream was reduced back to a low level and the Compound 2 obtained in Example 1 (1.5 g, 8.9 mmol) was added in one portion. The reaction mixture was heated between 50–55° C. After 30 min, an additional 1 g of Compound 2 was added. Thin-layer chromatography (TLC) indicated complete reaction after 1 hour. The reaction mixture was poured into saturated aqueous NaCl solution, extracted with ethyl acetate and the organic layer was dried over anhydrous MgSO$_4$. Concentration of the solvents followed by silica gel chromatography using hexane ethyl acetate (19:1) afforded 0.58 g (90%) of the title compound (Compound 4) as a colorless oil (mixture of diastereomers).

The proton nuclear magnetic resonance spectrum of the title compound (Compound 4) gave the following signal:

400 MHZ $^1$H NMR (CDCl$_3$) δ5.57 (1H), 5.31 (1H), 4.01 (1H), 3.65 (2H), 3.42–3.20 (2H), 2.90 (1H), 2.90 (1H), 2.77 (1H), 2.31 (2H), 1.31 (s×2, 3H), 1.28 (s×2, 3H), 1.19 (d×2, 3H), 0.88 (3H×7), 0.59 (s×2, 3H), 0.10 (3H), 0.06 (3H), 0.05 (3H), 0.00 (3H).

EXAMPLE 3

Synthesis of 1α,3β-bis(t-butyldimethylsilyloxy)-20 (R)-(2,3-epoxy-3-methylbutyloxy)pregn-5-ene

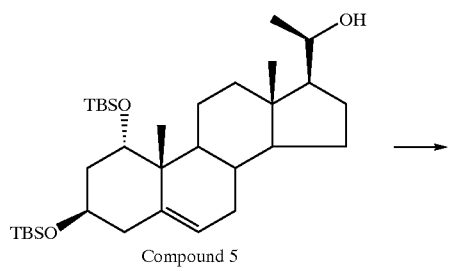

Compound 5

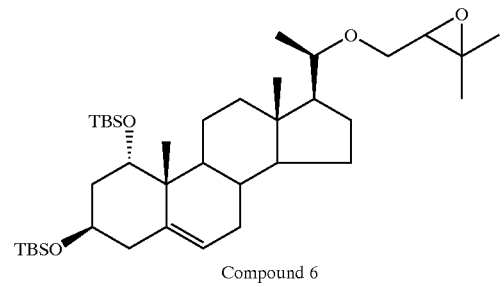

Compound 6

The alcohol Compound 5 (5.0 g, 8.88 mmol), 4-bromo-2,3-epoxy-2-methylbutane (2.2 g, 13.32 mmol), and then sodium hydride (dry 95%, 561 mg, 22.2 mmol) were added into a 100 ml round bottom eggplant type flask. THF (20 ml) was then added thereto. The reaction was performed under reflux for 2 hours. After cooling the reaction mixture, the reaction was quenched by addition of saturated aqueous NH$_4$Cl solution. The mixture was extracted with ethyl acetate and the organic layer was dried over MgSO$_4$ and concentrated. Isolation and purification by silica gel column chromatography using n-hexane/ethyl acetate (20:1) afforded 5.5 g (95.7%) of the title compound (Compound 6) as a white powder.

The proton nuclear magnetic resonance spectrum of the title compound (Component 6) gave the following signal:

270 MHz $^1$H NMR (δ: ppm) 5.42–5.44 (m,1H), 3.99–3.95 (m, 1H), 3.75 (br,1H), 3.71–3.61 (m,1H), 3.41–3.28 (m, 2H), 2.96–2.92 (t, 1H, J=5.61), 2.28–2.06 (m,3H), 1.32 (3H, s), 1.28–1.27 (3H), 1.10–1.06 (3H), 0.95 (3H,s), 0.86 (18H, s), 0.72–0.63 (3H), 0.04, 0.03, 0.02, 0.01 (12H, Si—CH$_3$):

EXAMPLE 4

Synthesis of 1α,3β-bis(t-butyldimethylsilyloxy)-20 (S)-(3-hydroxy-3-methylbutyloxy)pregna-5,7-diene

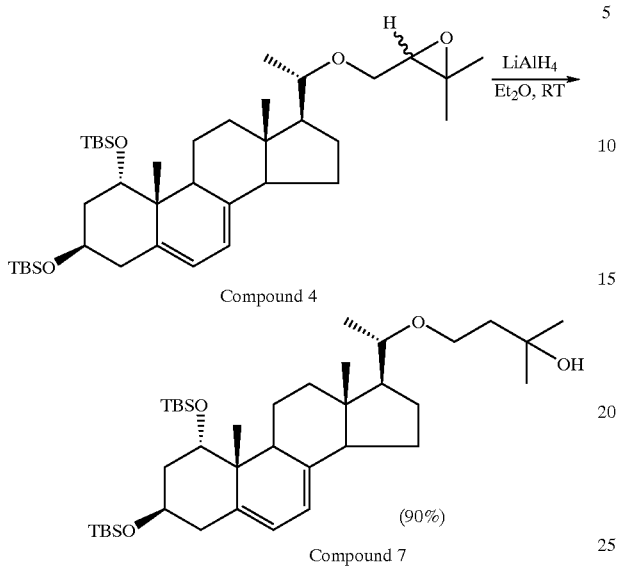

To a stirred solution of the epoxy steroid Compound 4 (obtained in Example 2, 200 mg, 0.3 mmol) in 20 mL of dry diethyl ether was added lithium aluminum hydride (LiAlH$_4$, 22 mg, 3.0 mmol) under argon at room temperature. Thin-layer chromatography (TLC) indicated complete and clean conversion of the starting material (Compound 4) after several hours. The reaction mixture was partitioned between 100 mL of ethyl acetate/saturated aqueous NaCl (1:1). The organic layer was separated and dried over anhydrous MgSO$_4$. Concentration and silica gel chromatography using hexane/ethyl acetate (9:1) afforded 582 mg (90%) of the title compound (Compound 7) as a colorless solid.

The proton nuclear magnetic resonance spectrum of the title compound (Compound 7) gave the following signal:

400 MHZ $^1$H NMR (CDCl$_3$): δ5.56 (1H), 5.30 (1H), 4.02 (1H), 3.82 (1H), 3.73 (1H, OH), 3.67 (1H), 3.47 (1H), 3.24 (1H), 2.75 (1H), 2.33 (2H), 1.22 (3H), 1.21 (3H), 1.18 (d, 3H), 0.88 (s, 3H), 0.86 (s, 3H×6), 0.59 (3H), 0.08 (s, 3H), 0.04 (s, 3H), 0.03 (s, 3H), 0.00(s, 3H).

EXAMPLE 5

One-pot synthesis of 1α,3β-bis(t-butyldimethylsilyloxy)-20(S)-(3-hydroxy-3-methylbutyloxy)pregn-5-ene

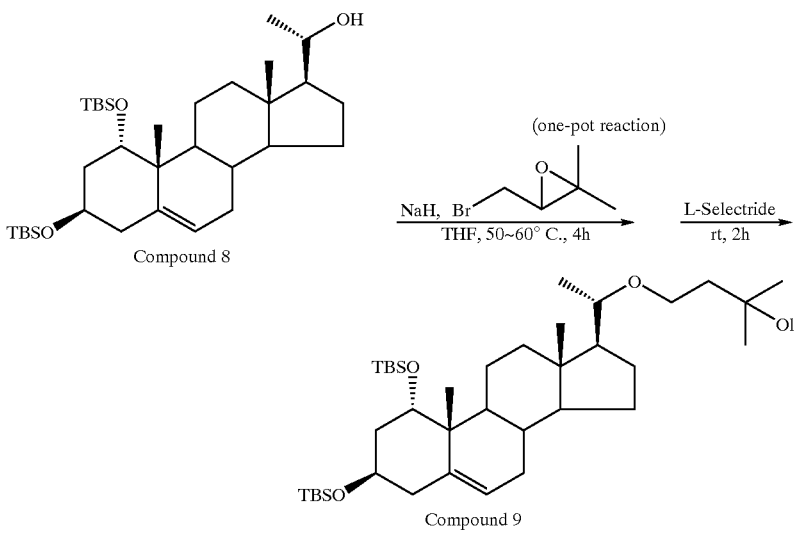

To a container were successively added the alcohol Compound 8 (0.5 g, 0.89 mmol), sodium hydride (60% oil dispersion, 71.2 mg, 1.78 mmol), THF (3 ml) and 4-bromo-2,3-epoxy-2-methylbutane (220 mg, 1.34 mmol). The mixture was stirred at a reaction temperature of 50–60° C. for 4 hours. After the reaction mixture was cooled to room temperature, 1.8 ml (1.8 mmol) of Li(s-Bu)$_3$BH (L-Selectride, 1.0 M solution in THF) was added to the mixture without its purification and reaction was performed at room temperature for 2 ours. The reaction was quenched by addition of saturated aqueous NH$_4$Cl-solution. The organic layer was washed with saturated aqueous NaHCO$_3$ solution, then with saturated aqueous NaCl solution, and the organic layer was dried over anhydrous MgSO$_4$. Concentration of the organic layer and purification by silica gel column chromatography using n-hexane/ethyl acetate (8:1) afforded 537 mg (93%) of the title compound (Compound 9).

270 MHz $^1$H (CDCl$_3$) δ6.43 (1H), 3.97 (1H), 3.82 (1H), 3.77 (1H), 3.75 (1H, OH), 3.46 (1H), 3.23 (1H), 2.27–2.14 (2H), 1.21 (6H), 1.17 (d, 3H, J=6.3 Hz), 0.94 (3H), 0.86 (9H), 0.65 (3H), 0.054 (3H), 0.036 (3H), 0.026 (3H), 0.006 (3H):

EXAMPLE 6

One-pot synthesis of 1α,3β-bis(t-butyldimethylsilyloxy)-20(S)-(3-hydroxy-3-methylbutyloxy)pregn-5-ene

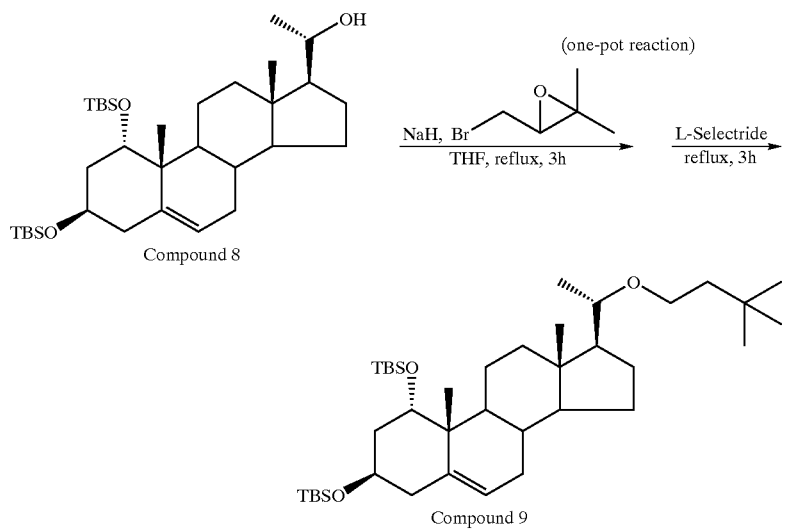

To a container were successively added sodium hydride (assay 95%, 179.5 g, 7.10 mol), THF (8 l), the alcohol Compound 8 (2 kg, 3.55 mol) and then 4-bromo-2,3-epoxy-2-methylbutane (762 g, 4.62 mol). The reaction was performed under reflux for 3 hours. After the reaction mixture was cooled to room temperature, Li(s-Bu)$_3$BH (L-Selectride, 9.9 l, 8.88 mol) was added thereto and the reaction was performed under reflux for 3 hours. Then, 3N aqueous NaOH solution and 35% aqueous hydrogen peroxide solution were successively added to the reaction mixture and the reaction was performed at room temperature for 2 hours. This reaction mixture was poured into aqueous Na$_2$S$_2$O$_3$ solution and the reaction was performed for 1 hour. The reaction mixture was washed with saturated aqueous NaHCO$_3$ solution, and then with saturated aqueous NaCl solution. After washing, the organic layer was concentrated and recrystallized from methanol to afford the title compound (2.16 kg, yield 93.7%).

EXAMPLE 7

One-pot synthesis of 1α,3β-bis(t-butyldimethylsilyloxy)-20(R)-(3-hydroxy-3-methylbutyloxy)pregn-5-ene

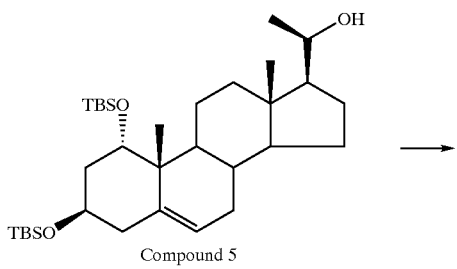

Compound 5

-continued

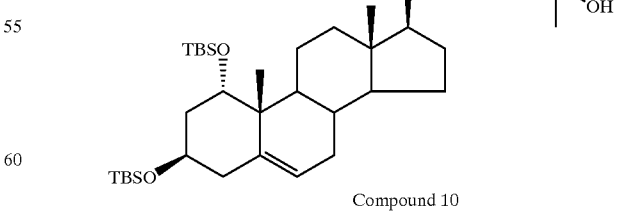

Compound 10

The alcohol Compound 5 (25 g, 44.4 mmol), sodium hydride (2.24 g), 4-bromo-2,3-epoxy-2-methylbutane (9.5 g), and then THF (100 ml) were added into an eggplant type flask and the mixture was refluxed for 2.5 hours. After cooling the mixture, L-Selectride (1.0 M solution in THF, 100 ml) was added thereto and the reaction was performed under reflux for 2 hours. After cooling the reaction mixture, 3N NaOH aqueous solution (50 ml) was slowly added thereto, and then 35% $H_2O_2$ solution (150 ml) was slowly added dropwise. After addition, the mixture was stirred for 1 hour. 20% $Na_2S_2O_3$ aqueous solution (100 ml) was then added and the mixture was stirred for 1 hour.

After the mixture was partitioned, the organic layer was washed with saturated NaCl aqueous solution (100 ml×3) and dried over anhydrous $MgSO_4$. $MgSO_4$ was filtered off and the organic layer was concentrated in vacuo. Acetonitrile (300 ml) was added thereto. The mixture was refluxed, and then cooled to room temperature to cause a crystallization. The resultant crystal was filtered and dried to afford 25.0 g (86.7%) of the title compound (Compound 10) as a white crystal.

270 MHz $^1$H NMR (δ: ppm) 5.45–5.43 (1H, m), 4.02–3.94 (1H, m), 3.85–3.76 (1H, m), 3.78–3.76 (1H, m), 3.48–3.41 (1H, m), 3.29–3.23 (1H, m), 1.23 (3H, s), 1.22 (3H, s), 1.12–1.09 (3H, d, J=5.94 Hz), 0.95 (3H, s), 0.87 (9H, s, t-Bu-Si), 0.86 (9H, s, t-Bu-Si), 0.69 (3H, s), 0.05 (3H, s, Si—$CH_3$), 0.04 (3H, s, Si—$CH_3$), 0.03 (3H, s, Si—$CH_3$), 0.01 (3H, s, Si—$CH_3$)

EXAMPLES 8–21

Test for the Reaction of the Epoxy Compound with Various Reducing Agents

As in example 5, the alcohol Compound 8 (0.5 g, 0.89 mmol), sodium hydride (60% oil dispersion, 71.2 mg, 1.78 mmol), THF (3 ml) and 4-bromo-2,3-epoxy-2-methylbutane (220 mg, 1.34 mmol) were successively added to a container. The mixture was stirred at a reaction temperature of 50–60° C. for 4 hours. The reaction was quenched by addition of saturated aqueous NaCl solution. The reaction mixture was extracted with ethyl acetate and the organic layer was dried over anhydrous $MgSO_4$. Concentration of the organic layer and purification by silica gel column chromatography using n-hexane/ethyl acetate (20:1) afforded the Compound 8'.

Then, each of the reducing agent under test was added to the container where the above-obtained epoxy compound (Compound 8') (100 mg, 0.155 mmol) is charged, and the reaction was effected under the conditions described in the following Table 1. After working-up the reaction mixture, the percent conversion to product(s) and the production ratio of the 25-hydroxy compound (Compound 9, end product) and the 24-hydroxy compound (Compound 11, by-product) were determined by high performance liquid chromatography (HPLC).

The results obtained are shown in Table 1.

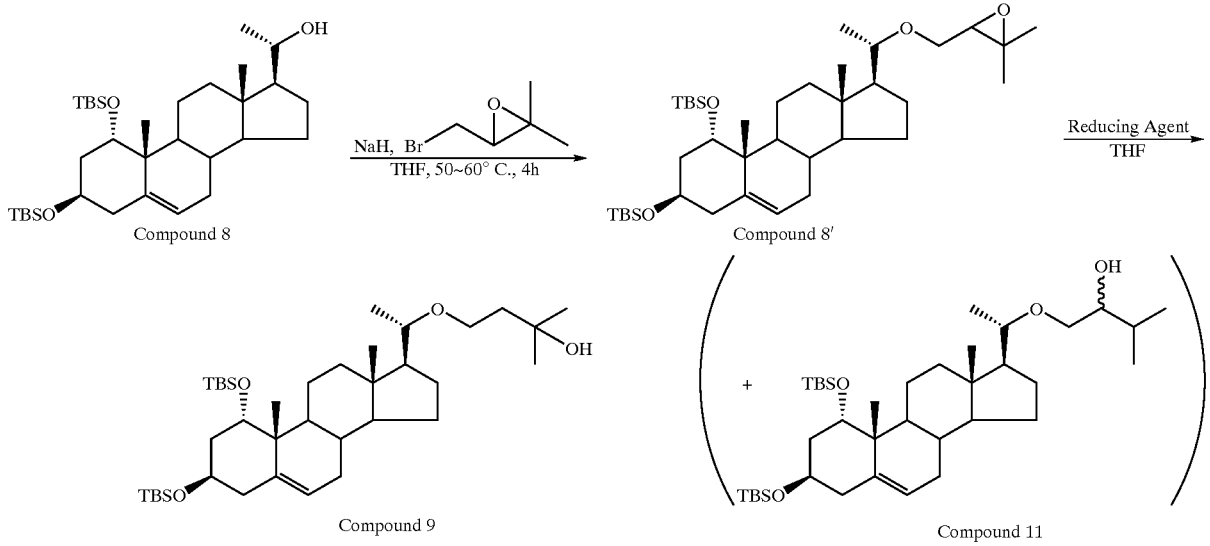

TABLE 1

| Ex. No. | Reducing Agent (eq.) | additive (eq.) | Temp. (° C.) | Time (hour) | Conversion[b] (%) | Ratio[a)b)] |
|---|---|---|---|---|---|---|
| 8 | $LiAlH_4$ (LAH) (3) | | r.t. | 4 | 93.5 | 92.6:7.4 |
| 9 | $LiAlH_4$ (LAH) (3) | | 50–60 | 4 | >99 | 75.3:24.7 |
| 10 | $NaBH_4$ (10) | | reflux | 5 | 5.3 | —[c] |
| 11 | $NaBH_3CN$ (5) | | reflux | 4 | No reaction | — |
| 12 | $NaBH_3CN$ (10) | $BF_3 \cdot OEt_2$ (2) | r.t. | 18 | 66.2 | —[d] |

TABLE 1-continued

| Ex. No. | Reducing Agent (eq.) | additive (eq.) | Temp. (°C.) | Time (hour) | Conversion[b] (%) | Ratio[a)b)] |
|---|---|---|---|---|---|---|
| 13 | NaBH$_3$CN (10) | AlCl$_3$ (1) | r.t. | 3.5 | 73.2 | —[c] |
| 14 | LiEt$_3$BH (5) (Super Hydride) | | r.t. | 3 | >99 | 98.2:1.8 |
| 15 | LiEt$_3$BH (5) (Super Hydride) | | 50—60 | 1 | >99 | 98.4:1.6 |
| 16 | LiB[CH(CH$_3$)C$_2$H$_5$]$_3$H (10) (L-Selectride) | | r.t. | 2.5 | >99 | 99.6:0.4[f] |
| 17 | KB(Sia)$_3$H (10) (KS-Selectride) | | r.t. | 18 | No reaction | — |
| 18 | KB(Sia)$_3$H (10) (KS-Selectride) | | reflux | 8 | 4.2 | — |
| 19 | KB(C$_6$H$_5$)$_3$H (10) | | r.t. | 18 | 2.8 | — |
| 20 | Lithium 9-BBN hydride | | r.t. | 27 | >99 | 99.3:0.7 |
| 21 | K(s-Bu)$_3$BH (10) (K-Selectride) | LiI (20) | r.t. | 23 | >99 | 99.4:0.6 | a) Production ratio of desired compound (compound 9): by-product (compound 11).
b) Determined by HPLC.
c) The desired compound 9 was produced in approximately 5% yield and the b-product compound 11 was also slightly produced.
d) The by-product compound 11 was produced in 28.3% yield and the desired compound 9 was not produced. Two other unknown materials were produced.
e) The by-product compound 11 was produced in 42% yield and the desired compound 9 was not produced. Other unknown materials were produced in 31.2% yield.
f) After isolation and purification by silica gel column chromatography, it was confirmed by NMR measurement that the resultant compound was the desired compound 9.

Note: r.t. means room temperature.

As understood from the above data, it was possible to complete the reaction and synthesize a desired compound with high selectivity for the position of reduction according to the process of the present invention.

EXAMPLE 22

Synthesis of (1S,3R,20S)-1,3-bis(tert-butyldimethylsilyloxy)-(2,3-epoxy-3-methylbutyloxy)-pregn-5-ene

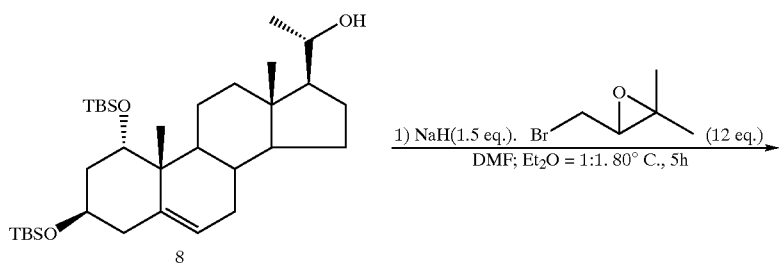

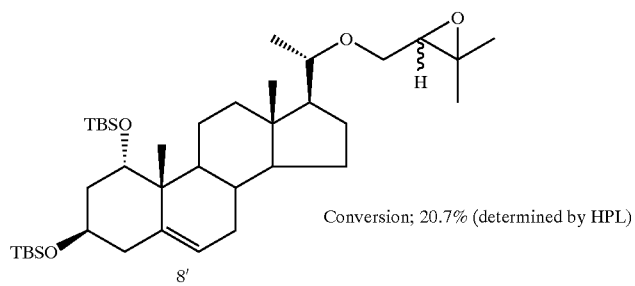

To a solution of alcohol (8) (1.0 g, 1.78 mmol) in DMF:Et$_2$O=1:1 (40 ml), sodium hydride (67 mg, 2.66 mmol) and 4-bromo-2,3-epoxy-2-methylbutane (3.5 g, 21.3 mmol) were added at room temperature. The reaction mixture was heated at 80° C. with vigorous stirring for 5 h, and then quenched with brine. The conversion was determined by reversed-phase HPLC (8'; 20.7%).

EXAMPLE 23

Synthesis of (1S,3R,20S)-1,3-bis(tert-butyldimethylsilyloxy)-(2,3-epoxy-3-methylbutyloxy)pregn-5-ene

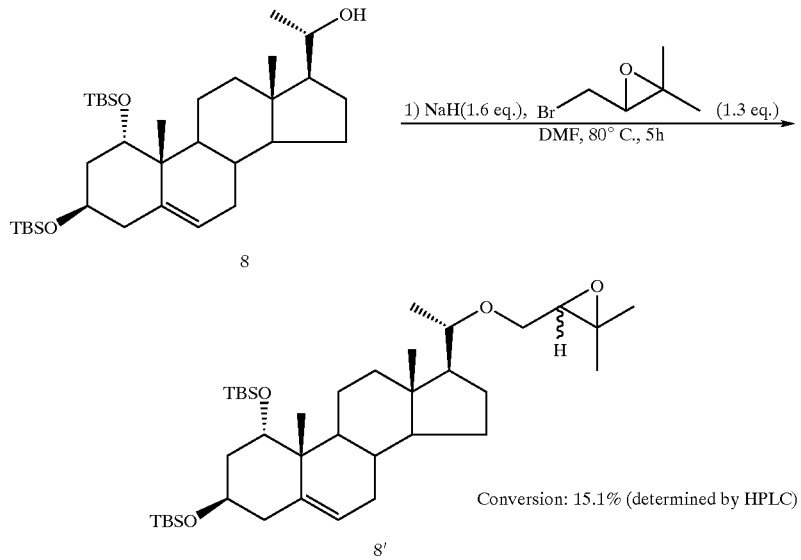

To a solution of alcohol (8) (1.0 g, 1.78 mmol) in DMF (5 ml), sodium hydride (67 mg, 2.66 mmol) and 4-bromo-2,3-epoxy-2-methylbutane (0.38 g, 2.31 mmol) were added at room temperature. The reaction mixture was heated at 80° C. with vigorous stirring for 5 h, and then quenched with brine. The conversion was determined by reversed-phase HPLC (8'; 15.1%).

EXAMPLE 24

Synthesis of (1S,3R,20S)-1,3-bis(tert-butyldimethylsilyloxy)-(2,3-epoxy-3-methylbutyloxy)pregn-5-ene

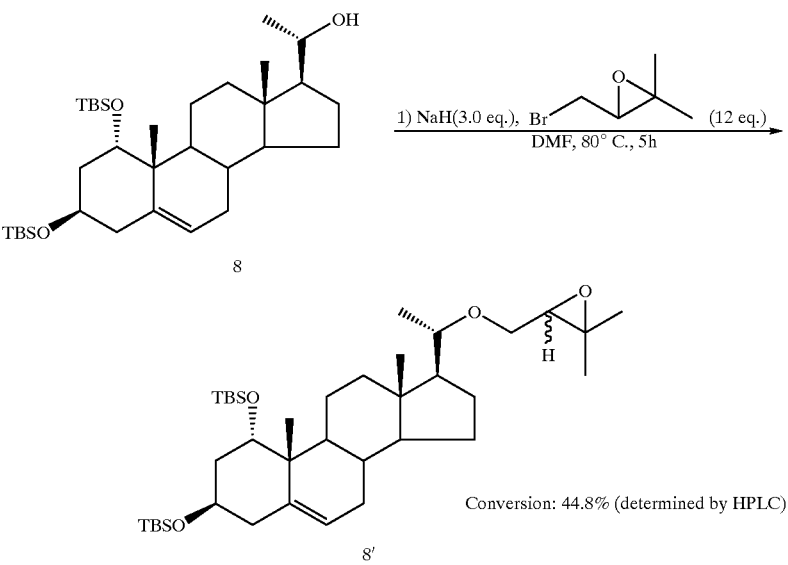

To a solution of alcohol (8) (1.0 g, 1.78 mmol) in DMF (5 ml), sodium hydride (90 mg, 5.34 mmol) and 4-bromo-2,3-epoxy-2-methylbutane (0.44 g, 2.67 nmol) were added at room temperature. The reaction mixture was heated at 80° C. with vigorous stirring for 2 h. After 2 h, an additional portion of 4-bromo-2,3-epoxy-2-methylbutane (0.44 g, 2.67 mmol) was added. After another 1 h, 0.88 g of 4-bromo-2,3-epoxy-2-methylbutane (5.34 mmol) was added at 80° C. Moreover after 1 h, 1.76 g of 4-bromo-2,3-epoxy-2-methylbutane (10.7 nmol) was added at 80° C. The reaction mixture was heated at 80° C. with vigorous stirring for 2 h, and then quenched with brine. The conversion was determined by reversed-phase HPLC (8'; 44.8%).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. A process for preparing a compound having the structure:

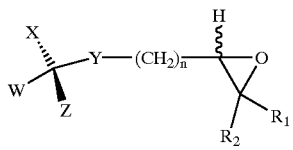

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is a CD ring structure of the formula

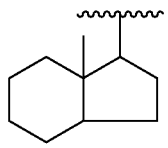

a steroid ring structure of the formula

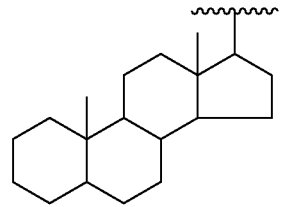

or a vitamin D structure of the formula

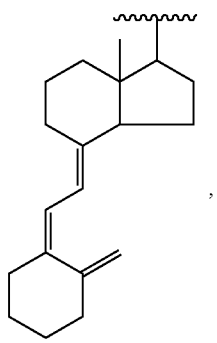

wherein each of the structures of Z optionally have one or more protected or unprotected substituents and/or one or more protective groups, and wherein any ring of the structure of Z may optionally have one or more unsaturated bonds;

which comprises:

a) reacting a compound having the structure:

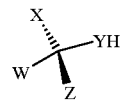

wherein W, X, Y and Z are as defined above, in the presence of a base, with a compound having the structure:

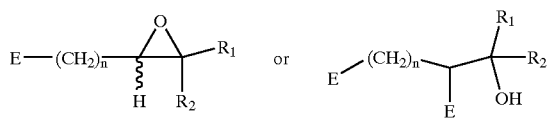

wherein n, $R_1$ and $R_2$ are as defined above, and E is an eliminating group, to produce the compound; and b) recovering the compound so produced.

2. The process of claim 1 wherein Z is:

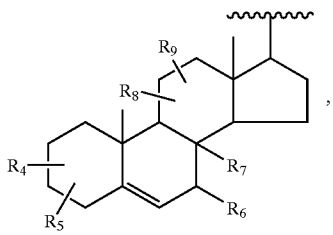

-continued

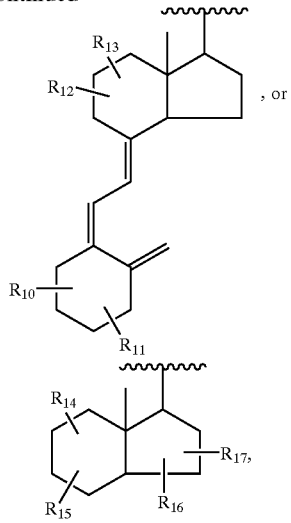, or

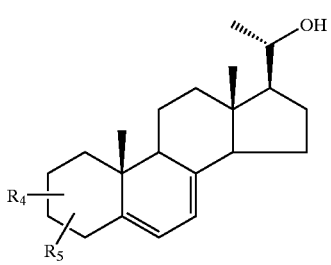

where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond.

3. The process of claim 1 for preparing a compound having the structure:

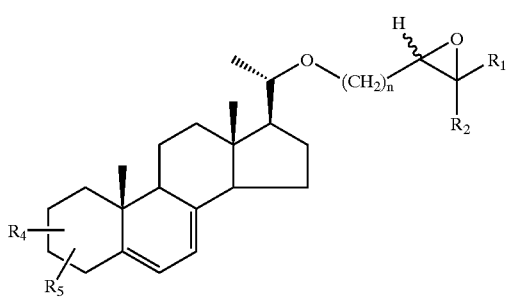

which comprises:

(a) reacting a compound having the structure:

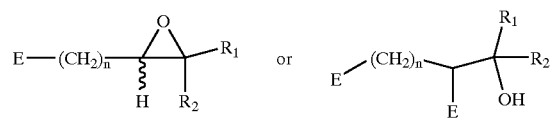

in the presence of a base, with a compound having the structure:

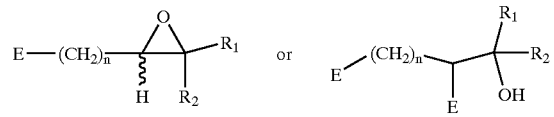

to produce the compound; and (b) recovering the compound so produced.

4. The process of claim 1 for preparing a compound having the structure:

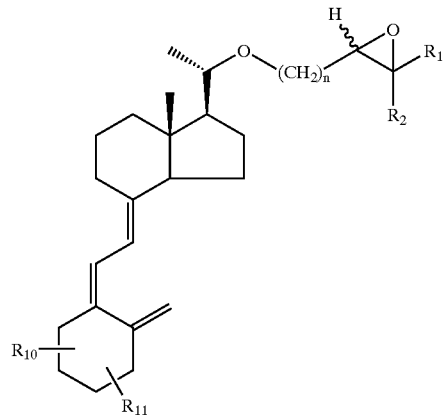

which comprises:

(a) reacting a compound having the structure:

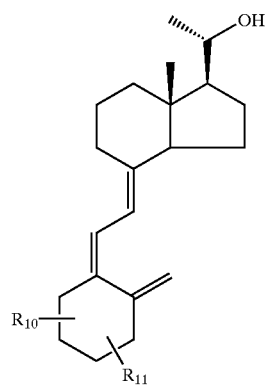

in the presence of a base, with a compound having the structure:

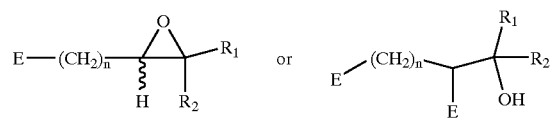

to produce the compound; and (b) recovering the compound so produced.

5. The process of claim 1 for preparing a compound having the structure:

49 which comprises:

(a) reacting a compound having the structure:

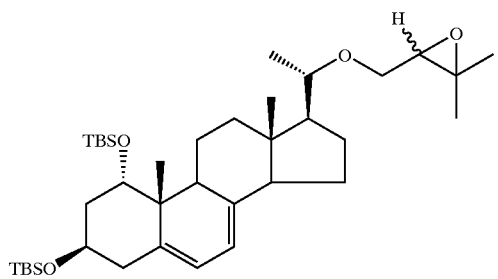

in the presence of a base, with a compound having the structure:

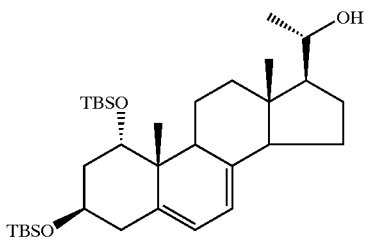

to produce the compound; and b) recovering the compound so produced.

6. The process of claim 1 for preparing a compound having the structure:

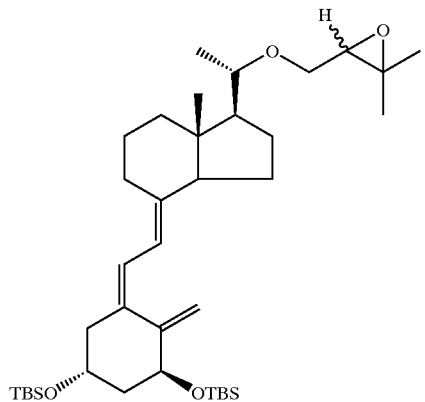

which comprises:

50

(a) reacting a compound having the structure:

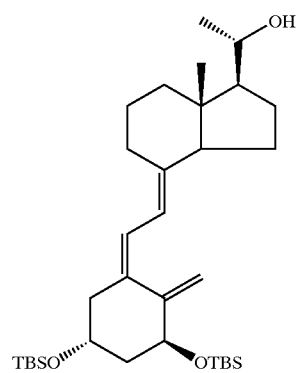

in the presence of a base, with a compound having the structure:

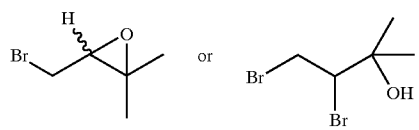

to produce the compound; and b) recovering the compound so produced.

7. The process of claim 1, where recovery of the compound comprises filtration or chromatography.

8. The process of claim 1, wherein the eliminating group E is halogen, mesyl, tosyl, imidate, trifluoromethanesulfonyl, or phenylsulfonyl.

9. The process of claim 8, wherein the halogen is bromine.

10. The process of claim 1, wherein the base is alkali metal hydride, alkali metal hydroxide, or alkali metal alkoxide.

11. The process of claim 10, wherein the alkali metal hydride is NaH or KH.

12. The process of claim 1, wherein the base is $NaOR_{20}$, $KOR_{20}$, $R_{20}Li$, $NaN(R_{21})_2$, $KN(R_{21})_2$, or $LiN(R_{21})_2$; $R_{20}$ is alkyl; and $R_{21}$ is isopropyl or $(CH_3)_3Si$.

13. A process for preparing a compound having the structure:

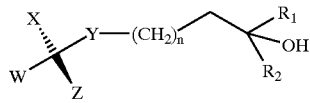

wherein n is an integer from 1–5; each of $R_1$ and $R_2$ independently is optionally substituted $C_1$–$C_6$ alkyl; each of W and X is independently hydrogen or $C_1$–$C_6$ alkyl; Y is O, S or $NR_3$ where $R_3$ is hydrogen, $C_1$–$C_6$ alkyl or a protective group; and Z is a CD ring structure of the formula

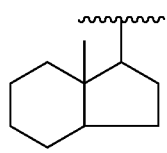

a steroid ring structure of the formula

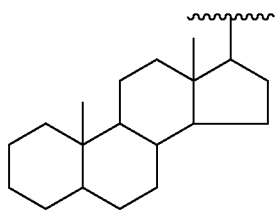

or a vitamin D structure of the formula

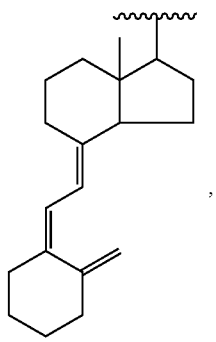

, wherein each of the structures of Z optionally have one or more protected or unprotected substituents and/or one or more protective groups, and wherein any ring of the structure of Z may optionally have one or more unsaturated bonds;
which comprises:
(a) reacting a compound having the structure:

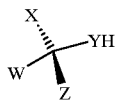

wherein W, X, Y and Z are as defined above, in the presence of a base, with a compound having the structure:

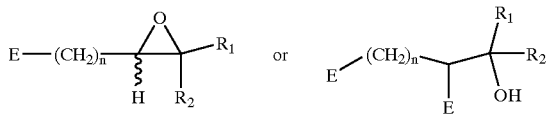

wherein n, $R_1$ and $R_2$ are as defined above, and E is an eliminating group, to produce an epoxide compound having the structure:

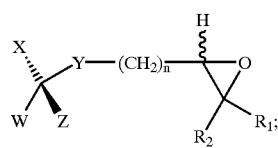

(b) treating the epoxide compound with a reducing agent to produce the compound; and
(c) recovering the compound so produced.

14. The process of claim 13 wherein Z is:

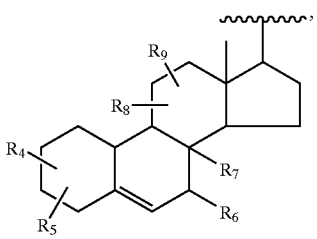

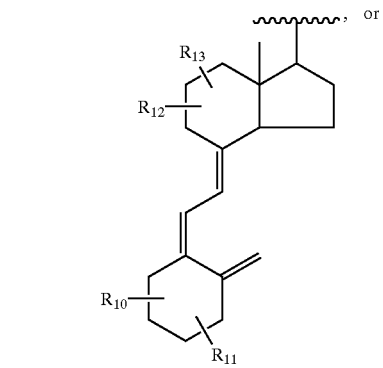

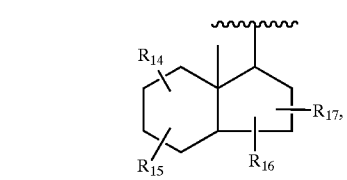

where each of $R_4$, $R_5$, $R_8$, $R_9$, $R_{10}$, $R_{11}$, $R_{12}$, $R_{13}$, $R_{14}$, $R_{15}$, $R_{16}$, and $R_{17}$ independently is hydrogen, a substituted or unsubstituted lower alkyloxy, amino, alkyl, alkylidene, carbonyl, oxo, hydroxyl, or protected hydroxyl; and each of $R_6$ and $R_7$ independently is hydrogen, substituted or unsubstituted lower alkyloxy, amino, alkyl, alkylidene, carbonyl, oxo, hydroxyl, protected hydroxyl, or together constitute a double bond.

15. The process of claim 13 for preparing a compound having the structure:

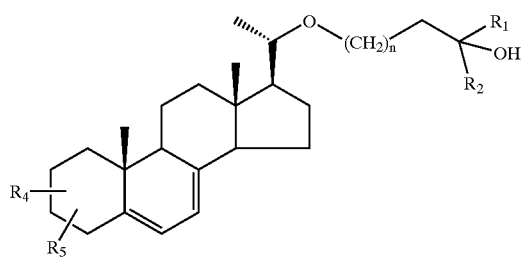

which comprises:

53 a) reacting a compound having the structure:

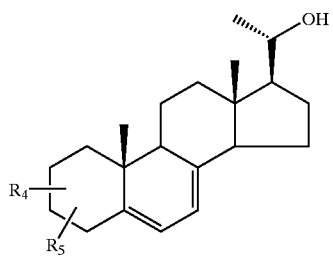

in the presence of a base, with a compound having the structure:

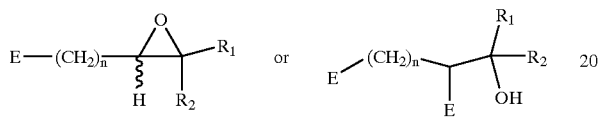

to produce an epoxide compound having the structure:

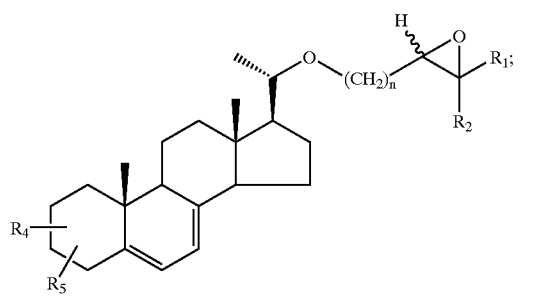

(b) treating the epoxide compound with a reducing agent to produce the compound; and (c) recovering the compound so produced.

16. The process of claim 13 for preparing a compound having the structure:

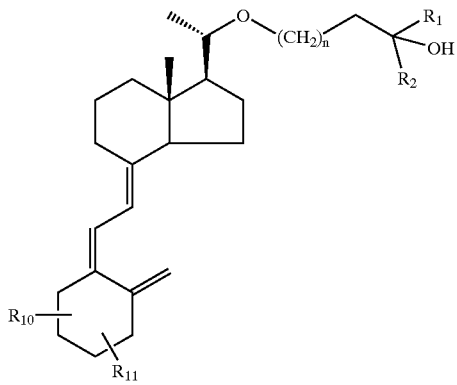

which comprises:

54 a) reacting a compound having the structure:

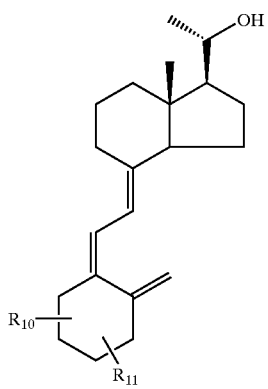

in the presence of a base, with a compound having the structure:

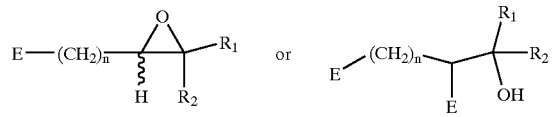

to produce an epoxide compound having the structure:

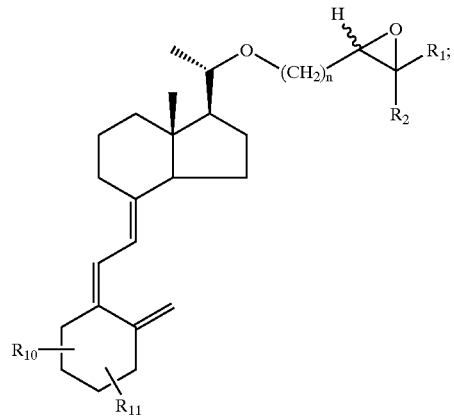

(b) treating the epoxide compound with a reducing agent to produce the compound; and (c) recovering the compound so produced.

17. The process of claim 13 for preparing a compound having the structure:

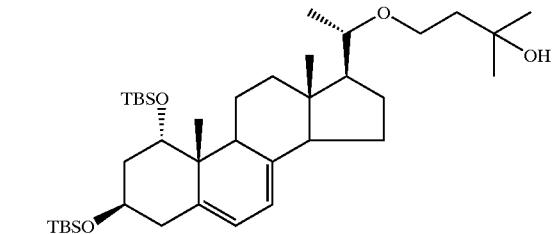

which comprises:

a) reacting a compound having the structure:

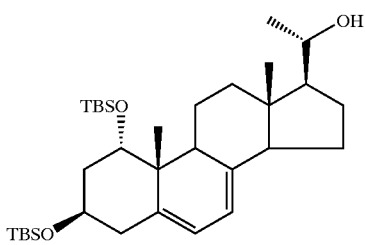

in the presence of a base, with a compound having the structure:

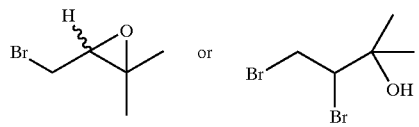

to produce an epoxide compound having the structure:

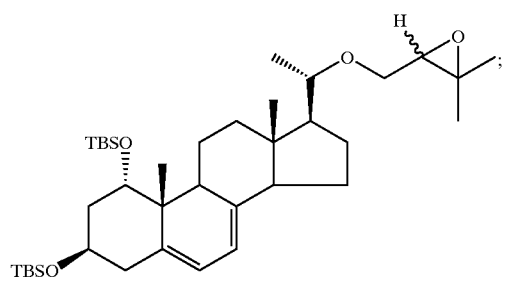

(b) treating the epoxide compound with a reducing agent to produce the compound; and (c) recovering the compound so produced.

18. The process of claim 13 for preparing a compound having the structure:

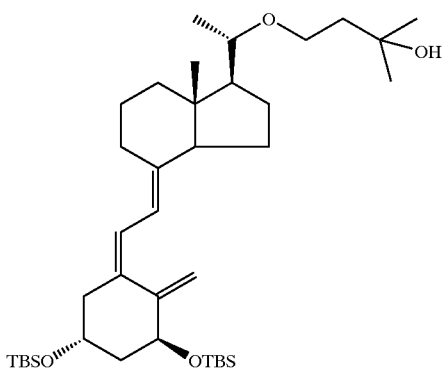

which comprises:

(a) reacting a compound having the structure:

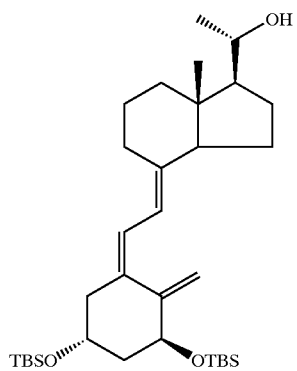

in the presence of a base, with a compound having the structure:

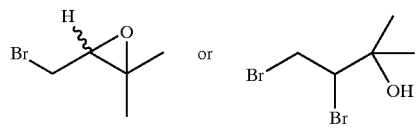

to produce an epoxide compound having the structure:

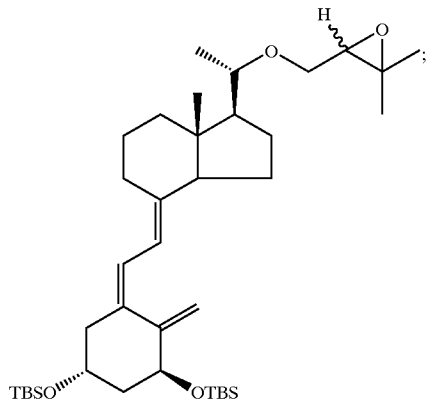

(b) treating the epoxide compound with a reducing agent to produce the compound; and (c) recovering the compound so produced.

19. The process of claim 13, where recovery of the compound comprises filtration or chromatography.

20. The process of claim 13, wherein the eliminating group is halogen, mesyl, tosyl, imidate, trifluoromethanesulfonyl, or phenylsulfonyl.

21. The process of claim 20, wherein the halogen is bromine.

22. The process of claim 13, wherein the base is alkali metal hydride, alkali metal hydroxide, or alkali metal alkoxide.

23. The process of claim 22, wherein the alkali metal hydride is NaH or KH.

24. The process of claim 13, wherein the base is $NaOR_{20}$, $KOR_{20}$, $R_{20}Li$, $NaN(R_{21})_2$, $KN(R_{21})_2$, or $LiN(R_{21})_2$; $R_{20}$ is alkyl; and $R_{21}$ is isopropyl or $(CH_3)_3Si$.

25. The process of claim 13, wherein the reducing agent is $LiAlH_4$, $Li(s-Bu)_3BH$, or $LiEt_3BH$.

26. The process of claim 13, wherein said step (b) is accomplished without separating the epoxide compound produced in step (a) from the reaction products of step (a).

27. The process of claim 26, wherein said steps (a) and (b) take place in the presence of tetrahydrofuran as a solvent.

28. The process of claim 27, wherein said reducing agent is selected from the group consisting of lithium tri-sec-butylborohydride, potassium tri-sec-butylborohydride, lithium triethylborohydride, and lithium 9-BBN hydride.

29. The process of claim 1 wherein n=1.

30. The process of claim 13 wherein n=1.

* * * * *